(12) United States Patent
Kim et al.

(10) Patent No.: US 11,965,186 B2
(45) Date of Patent: Apr. 23, 2024

(54) NUCLEIC ACID-GUIDED NICKASES

(71) Applicant: Inscripta, Inc., Boulder, CO (US)

(72) Inventors: Juhan Kim, Boulder, CO (US); Benjamin Mijts, Boulder, CO (US)

(73) Assignee: Inscripta, Inc., Pleasanton, CA (US)

( * ) Notice: Subject to any disclaimer, the term of this patent is extended or adjusted under 35 U.S.C. 154(b) by 273 days.

(21) Appl. No.: 17/676,218

(22) Filed: Feb. 20, 2022

(65) Prior Publication Data

US 2022/0213457 A1 Jul. 7, 2022

Related U.S. Application Data

(63) Continuation of application No. 17/463,581, filed on Sep. 1, 2021, now Pat. No. 11,268,078.

(60) Provisional application No. 63/133,502, filed on Jan. 4, 2021.

(51) Int. Cl.
| | |
|---|---|
| *C12N 9/22* | (2006.01) |
| *C12N 15/11* | (2006.01) |
| *C12N 15/113* | (2010.01) |
| *C12N 15/90* | (2006.01) |

(52) U.S. Cl.
CPC ............... *C12N 9/22* (2013.01); *C12N 15/11* (2013.01); *C12N 15/907* (2013.01); *C12Y 301/21004* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,278 B2 | 5/2018 | Gill et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,240,167 B2 | 3/2019 | Gill et al. |
| 10,266,849 B2 | 4/2019 | Gill et al. |
| 10,266,851 B2 | 4/2019 | Chen |
| 10,337,028 B2 | 7/2019 | Gill et al. |
| 10,351,877 B2 | 7/2019 | Gill et al. |
| 10,364,442 B2 | 7/2019 | Gill et al. |
| 10,435,714 B2 | 10/2019 | Gill et al. |
| 10,435,715 B2 | 10/2019 | Gill et al. |
| 10,604,746 B1 | 3/2020 | Mijts et al. |
| 10,626,416 B2 | 4/2020 | Gill et al. |
| 10,640,754 B1 | 5/2020 | Mijts et al. |
| 10,665,114 B2 | 5/2020 | Irrgang et al. |
| 10,669,559 B2 | 6/2020 | Garst et al. |
| 10,689,669 B1 | 6/2020 | Feldman et al. |
| 10,704,033 B1 | 7/2020 | Kim et al. |
| 10,711,284 B2 | 7/2020 | Garst et al. |
| 10,724,021 B1 | 7/2020 | Kim et al. |
| 10,731,180 B2 | 8/2020 | Garst et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,870,761 B2 | 12/2020 | Spahr et al. |
| 10,876,102 B2 | 12/2020 | Mijts et al. |
| 10,883,077 B2 | 1/2021 | Belgrader et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharamyces cerevisiae*", Yeast, 35:201-11 (2018).

(Continued)

*Primary Examiner* — Suzanne M Noakes
*Assistant Examiner* — Jae W Lee
(74) *Attorney, Agent, or Firm* — Arnold & Porter Kaye Scholer LLP

(57) ABSTRACT

The present disclosure provides engineered nucleic acid-guided nickases and optimized scaffolds for making rational, direct edits to nucleic acids in live cells.

20 Claims, 16 Drawing Sheets

Specification includes a Sequence Listing.

(56) References Cited

U.S. PATENT DOCUMENTS

| | | |
|---|---|---|
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2018/0327761 A1 | 11/2018 | Duchateau et al. |
| 2018/0371498 A1 | 12/2018 | Gill et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0109398 A1 | 4/2020 | Rubens et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO2017/106414 | 6/2017 |
| WO | WO 2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/031950 | 2/2018 |
| WO | WO 2018/071672 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO2020/191102 | 9/2020 |
| WO | WO2020/191153 | 9/2020 |
| WO | WO2020/217057 | 10/2020 |
| WO | WO2021/207541 | 10/2021 |

OTHER PUBLICATIONS

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

Farasat et al., "A Biophysical Model of CRISPR/Cas9 Activity for Rational Design of Genome Editing and Gene Regulation," PLoS Comput Biol., 29:12(1):e1004724 (2016).

Liu et al., "A chemical-inducible CRISPR-Cas9 system for rapid control of genome editing", Nature Chemical Biology, 12:980-987(2016).

Eklund, et al., "Altered target site specificity variants of the I-Ppol His-Cys bis homing endonuclease" Nucleic Acids Research, 35(17):5839-50 (2007).

Boles, et al., "Digital-to-biological converter for on-demand production of biologics", Nature Biotechnology, doi:10.1038/nbt.3859 (May 29, 2017).

Pines, et al., "Codon Compression Algorithms for Saturation Mutagenesis", ACS Synthetic Biology, 4:604-14 (2015).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

Casini et al., "Bricks and blueprints: methods and standards for DNA assembly," Nat Rev Mol Cell Biol., (9):568-76 (2015).

Chica et al., "Semi-rational approaches to engineering enzyme activity: combining the benefits of directed evolution and rational design," Current Opinion in Biotechnology, 16(4): 378-384 (2005).

Durai et al., "Zinc finger nucleases: custom-designed molecular scissors for genome engineering of plant and mammalian cells", Nucleic Acids Res., 33(18):5978-90 (2005).

Kadonaga et al., "Regulation of RNA polymerase II transcription by sequence-specific DNA binding factors", Cell, 116(2):247-57 (2004).

Lee et al., "Targeted chromosomal deletions in human cells using zinc finger nucleases", Genome Res., 20 (1): 81-9 (2009).

Miller et al., "A TALE nuclease architecture for efficient genome editing", Nature Biotechnology, 29 (2): 143-8 (2011).

Mittelman et al., "Zinc-finger directed double-strand breaks within CAG repeat tracts promote repeat instability in human cells", PNAS USA, 106 (24): 9607-12 (2009).

(56) References Cited

OTHER PUBLICATIONS

Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9): e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
Parks et al., "A standarized bacterial taxonomy based on genome phylogeny substantially revises the tree of life," Nat. Biotechnol. 36, pp. 996-1004 (2018).
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.

(56) References Cited

OTHER PUBLICATIONS

Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS One, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi: 10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Anzalone, et al., "Programmable large DNA deletion, replacement, integration, and inversion with twin prime editing and site-specific recombinases", bioRxiv, Nov. 2, 2021, doi:10.1101/2021.11.01.466790, p. 1-51.
Horwitz, et al., "Efficient Multiplexed Integration of Synergistic Alleles and Metabolic Pathways in Yeasts via CRISPR-Cas", Cell Systems 1, Jul. 29, 2015, doi:10.1016/j.cels.2015.02.001, p. 88-96.
Jillette, et al., "Split Selectable Markers", Nature Communications, Oct. 31, 2019, doi:10.1038/s41467-019-12891-2, p. 1-8.
Pavankumar, "Inteins: Localized Distribution, Gene Regulation, and Protein Engineering for Biological Applications", Microorganisms, Feb. 28, 2018, doi:10.3390/microorganisms6010019, p. 1-15.
Choi, et al., "Precise genomic deletions using paired prime editing", bioRxiv, Jan. 2, 2021, doi:10.1101/2020.12.30.424891, p. 1-32.
Lin, et al., "High-efficiency prime editing with optimized, paired pegRNAs in plants", Nature Biotechnology, Mar. 25, 2021, doi:10.1038/s41587-021-00868-w, p. 1-12.
Bolukbasi, et al., "Orthogonal Cas9-Cas9 chimeras provide a versatile platform for genome editing", Nature Communications, Nov. 19, 2018, doi:10.1038/s41467-018-07310-x, p. 1-12.
Kweon, et al., "Fusion guide RNAs for orthogonal gene manipulation with Cas9 and Cpf1", Nature Communications, Nov. 23, 2017, doi:10.1038/s41467-017-01650-w, p. 1-6.
International Search Report and Written Opinion for International Application No. PCT/US21/48578, dated Feb. 15, 2022, p. 1-12.
International Search Report and Written Opinion for International Application No. PCT/US21/61156, dated Mar. 3, 2022, p. 1-13.

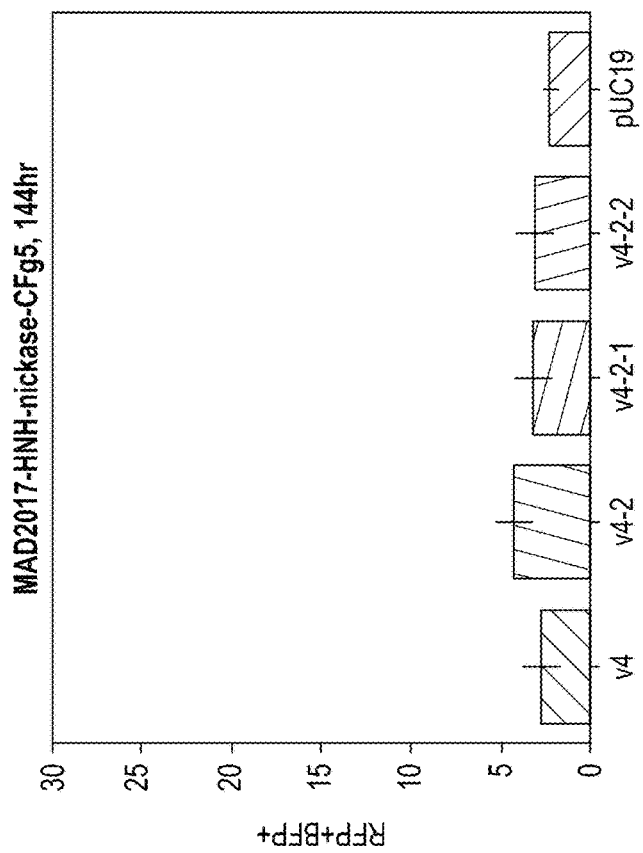
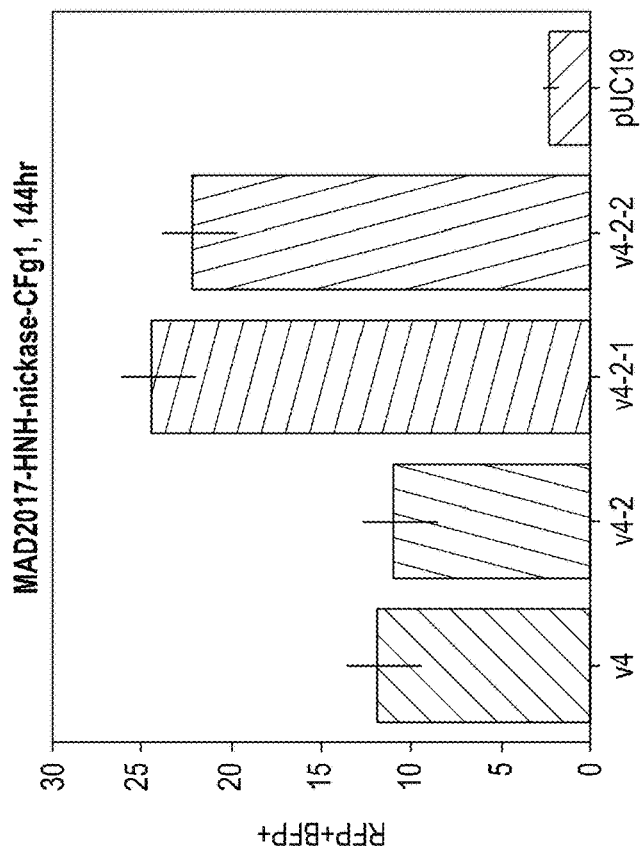
FIG. 6A
FIG. 6B

SEQUENCE LISTING

<160> NUMBER OF SEQ ID NOS: 32

<210> SEQ ID NO 1
<211> LENGTH: 1367
<212> TYPE: PRT
<213> ORGANISM: Streptococcus acidominimus

<400> SEQUENCE: 1

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Ala Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Lys Lys Tyr Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Ile Leu Thr Val Thr Asp Asn Gly Thr Glu Thr Pro Leu Ser Ser Ala
305                 310                 315                 320

Met Ile Met Arg Tyr Lys Glu His Glu Glu Asp Leu Gly Leu Leu Lys
                325                 330                 335

Ala Tyr Ile Arg Asn Ile Ser Leu Lys Thr Tyr Asn Glu Val Phe Asn
            340                 345                 350

Asp Asp Thr Lys Asn Gly Tyr Ala Gly Tyr Ile Asp Gly Lys Thr Asn
        355                 360                 365

```
Gln Glu Asp Phe Tyr Val Tyr Leu Lys Lys Leu Leu Ala Lys Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Thr Val Tyr Asn Glu Leu Thr Lys Val Arg
        515                 520                 525

Phe Ile Ala Glu Gly Met Ser Asp Tyr Gln Phe Leu Asp Ser Lys Gln
    530                 535                 540

Lys Lys Asp Ile Val Arg Leu Tyr Phe Lys Gly Lys Arg Lys Val Lys
545                 550                 555                 560

Val Thr Asp Lys Asp Ile Ile Glu Tyr Leu His Ala Ile Asp Gly Tyr
                565                 570                 575

Asp Gly Ile Glu Leu Lys Gly Ile Glu Lys Gln Phe Asn Ser Ser Leu
            580                 585                 590

Ser Thr Tyr His Asp Leu Leu Asn Ile Ile Asn Asp Lys Glu Phe Leu
        595                 600                 605

Asp Asp Ser Ser Asn Glu Ala Ile Ile Glu Glu Ile Ile His Thr Leu
    610                 615                 620

Thr Ile Phe Glu Asp Arg Glu Met Ile Lys Gln Arg Leu Ser Lys Phe
625                 630                 635                 640

Glu Asn Ile Phe Asp Lys Ser Val Leu Lys Lys Leu Ser Arg Arg His
                645                 650                 655

Tyr Thr Gly Trp Gly Lys Leu Ser Ala Lys Leu Ile Asn Gly Ile Arg
            660                 665                 670

Asp Glu Lys Ser Gly Asn Thr Ile Leu Asp Tyr Leu Ile Asp Asp Gly
        675                 680                 685

Ile Ser Asn Arg Asn Phe Met Gln Leu Ile His Asp Asp Ala Leu Ser
    690                 695                 700

Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
                725                 730                 735

Lys Lys Gly Ile Leu Gln Ser Ile Lys Ile Val Asp Glu Leu Val Lys
            740                 745                 750

Val Met Gly Arg Lys Pro Glu Ser Ile Val Val Glu Met Ala Arg Glu
        755                 760                 765

Asn Gln Tyr Thr Asn Gln Gly Lys Ser Asn Ser Gln Gln Arg Leu Lys
    770                 775                 780

Arg Leu Glu Glu Ser Leu Glu Glu Leu Gly Ser Lys Ile Leu Lys Glu
```

```
                      785                 790                 795                 800
Asn Ile Pro Ala Lys Leu Ser Lys Ile Asp Asn Asn Ser Leu Gln Asn
                  805                 810                 815

Asp Arg Leu Tyr Leu Tyr Tyr Leu Gln Asn Gly Lys Asp Met Tyr Thr
                  820                 825                 830

Gly Asp Asp Leu Asp Ile Asp Arg Leu Ser Asn Tyr Asp Ile Asp His
                  835                 840                 845

Ile Ile Pro Gln Ala Phe Leu Lys Asp Asn Ser Ile Asp Asn Lys Val
        850                 855                 860

Leu Val Ser Ser Ala Ser Asn Arg Gly Lys Ser Asp Asp Val Pro Ser
865                 870                 875                 880

Leu Glu Val Val Lys Lys Arg Lys Thr Leu Trp Tyr Gln Leu Leu Lys
                    885                 890                 895

Ser Lys Leu Ile Ser Gln Arg Lys Phe Asp Asn Leu Thr Lys Ala Glu
                900                 905                 910

Arg Gly Gly Leu Ser Pro Glu Asp Lys Ala Gly Phe Ile Gln Arg Gln
                915                 920                 925

Leu Val Glu Thr Arg Gln Ile Thr Lys His Val Ala Arg Leu Leu Asp
                930                 935                 940

Glu Lys Phe Asn Asn Lys Lys Asp Glu Asn Asn Arg Ala Val Arg Thr
945                 950                 955                 960

Val Lys Ile Ile Thr Leu Lys Ser Thr Leu Val Ser Gln Phe Arg Lys
                965                 970                 975

Asp Phe Glu Leu Tyr Lys Val Arg Glu Ile Asn Asp Phe His His Ala
                980                 985                 990

His Asp Ala Tyr Leu Asn Ala Val Val Ala Ser Ala Leu Leu Lys Lys
            995                1000                1005

Tyr Pro Lys Leu Glu Pro Glu Phe Val Tyr Gly Asp Tyr Pro Lys
        1010                1015                1020

Tyr Asn Ser Phe Arg Glu Arg Lys Ser Ala Thr Glu Lys Val Tyr
        1025                1030                1035

Phe Tyr Ser Asn Ile Met Asn Ile Phe Lys Lys Ser Ile Ser Leu
        1040                1045                1050

Ala Asp Gly Arg Val Ile Glu Arg Pro Leu Ile Glu Val Asn Glu
        1055                1060                1065

Glu Thr Gly Glu Ser Val Trp Asn Lys Glu Ser Asp Leu Ala Thr
        1070                1075                1080

Val Arg Arg Val Leu Ser Tyr Pro Gln Val Asn Val Val Lys Lys
        1085                1090                1095

Val Glu Val Gln Ser Gly Gly Phe Ser Lys Glu Leu Val Gln Pro
        1100                1105                1110

His Gly Asn Ser Asp Lys Leu Ile Pro Arg Lys Thr Lys Lys Met
        1115                1120                1125

Ile Trp Asp Thr Lys Lys Tyr Gly Gly Phe Asp Ser Pro Ile Val
        1130                1135                1140

Ala Tyr Ser Val Leu Val Met Ala Glu Arg Glu Lys Gly Lys Ser
        1145                1150                1155

Lys Lys Leu Lys Pro Val Lys Glu Leu Val Arg Ile Thr Ile Met
        1160                1165                1170

Glu Lys Glu Ser Phe Lys Glu Asn Thr Ile Asp Phe Leu Glu Arg
        1175                1180                1185

Arg Gly Leu Arg Asn Ile Gln Asp Glu Asn Ile Ile Leu Leu Pro
        1190                1195                1200
```

```
Lys Phe Ser Leu Phe Glu Leu Glu Asn Gly Arg Arg Arg Leu Leu
    1205                1210                1215

Ala Ser Ala Lys Glu Leu Gln Lys Gly Asn Glu Phe Ile Leu Pro
    1220                1225                1230

Asn Lys Leu Val Lys Leu Leu Tyr His Ala Lys Asn Ile His Asn
    1235                1240                1245

Thr Leu Glu Pro Glu His Leu Glu Tyr Val Glu Ser His Arg Ala
    1250                1255                1260

Asp Phe Gly Lys Ile Leu Asp Val Val Ser Val Phe Ser Glu Lys
    1265                1270                1275

Tyr Ile Leu Ala Glu Ala Lys Leu Glu Lys Ile Lys Glu Ile Tyr
    1280                1285                1290

Arg Lys Asn Met Asn Thr Glu Ile His Glu Met Ala Thr Ala Phe
    1295                1300                1305

Ile Asn Leu Leu Thr Phe Thr Ser Ile Gly Ala Pro Ala Thr Phe
    1310                1315                1320

Lys Phe Phe Gly His Asn Ile Glu Arg Lys Arg Tyr Ser Ser Val
    1325                1330                1335

Ala Glu Ile Leu Asn Ala Thr Leu Ile His Gln Ser Val Thr Gly
    1340                1345                1350

Leu Tyr Glu Thr Arg Ile Asp Leu Gly Lys Leu Gly Glu Asp
    1355                1360                1365

<210> SEQ ID NO 2
<211> LENGTH: 1375
<212> TYPE: PRT
<213> ORGANISM: Streptococcus acidominimus

<400> SEQUENCE: 2

Met Lys Lys Pro Tyr Ser Ile Gly Leu Asp Ile Gly Thr Asn Ser
1               5                   10                  15

Gly Trp Ala Val Ile Thr Asp Asp Tyr Lys Val Pro Ala Lys Lys Met
                20                  25                  30

Lys Val Leu Gly Asn Thr Asp Lys Lys Tyr Ile Lys Lys Asn Leu Leu
            35                  40                  45

Gly Ala Leu Leu Phe Asp Ser Gly Glu Thr Ala Glu Val Thr Arg Leu
        50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Thr Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
        115                 120                 125

His Gln Lys Phe Pro Thr Ile Tyr His Leu Arg Lys Tyr Leu Ala Asp
    130                 135                 140

Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
                165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
```

```
                195                 200                 205
Ser Ser Ile Leu Thr Glu Lys Val Ser Lys Ser Arg Arg Leu Glu Asn
    210                 215                 220

Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
                245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
        275                 280                 285

Leu Phe Ile Ser Ala Lys Asn Leu Tyr Asp Ala Ile Leu Leu Ser Gly
    290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
                325                 330                 335

Glu Phe Ile Lys Ile Asn Lys Leu Lys Leu Tyr His Asp Ile Phe Lys
            340                 345                 350

Asp Lys Thr Lys Asn Gly Tyr Ala Gly Tyr Ile Asp Asn Gly Val Lys
        355                 360                 365

Gln Asp Glu Phe Tyr Lys Tyr Leu Lys Thr Ile Leu Thr Lys Ile Asp
    370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
                405                 410                 415

Gln Glu Met His Ser Ile Leu Arg Arg Gln Gly Glu Tyr Tyr Pro Phe
            420                 425                 430

Leu Lys Glu Asn Gln Ala Lys Ile Glu Lys Ile Leu Thr Phe Arg Ile
        435                 440                 445

Pro Tyr Tyr Val Gly Pro Leu Ala Arg Lys Asp Ser Arg Phe Ala Trp
    450                 455                 460

Ala Asn Tyr His Ser Asp Glu Pro Ile Thr Pro Trp Asn Phe Asp Glu
465                 470                 475                 480

Val Val Asp Lys Glu Lys Ser Ala Glu Lys Phe Ile Thr Arg Met Thr
                485                 490                 495

Leu Asn Asp Leu Tyr Leu Pro Glu Glu Lys Val Leu Pro Lys His Ser
            500                 505                 510

His Val Tyr Glu Thr Phe Thr Val Tyr Asn Glu Leu Thr Lys Ile Lys
        515                 520                 525

Tyr Val Asn Glu Gln Gly Glu Ser Phe Phe Asp Ala Asn Met Lys
    530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
                565                 570                 575

Asn Asp Leu Ile Gly Leu Asp Lys Asp Ser Lys Ser Phe Asn Ala Ser
            580                 585                 590

Leu Gly Thr Tyr His Asp Leu Lys Lys Ile Leu Asp Lys Ser Phe Leu
        595                 600                 605

Asp Asp Lys Thr Asn Glu Gln Ile Ile Glu Asp Ile Val Leu Thr Leu
    610                 615                 620
```

```
Thr Leu Phe Glu Asp Arg Asp Met Ile His Glu Arg Leu Gln Lys Tyr
625                 630                 635                 640

Ser Asp Phe Phe Thr Ser Gln Gln Leu Lys Leu Glu Arg Arg His
            645                 650                 655

Tyr Thr Gly Trp Gly Arg Leu Ser Tyr Lys Leu Ile Asn Gly Ile Arg
            660                 665                 670

Asn Lys Glu Asn Asn Lys Thr Ile Leu Asp Phe Leu Ile Asp Asp Gly
            675                 680                 685

His Ala Asn Arg Asn Phe Met Gln Leu Ile Asn Asp Glu Ser Leu Ser
690                 695                 700

Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
                725                 730                 735

Gly Ile Leu Gln Ser Val Lys Ile Val Asp Glu Leu Val Lys Val Met
            740                 745                 750

Gly Asp Asn Pro Asp Asn Ile Val Ile Glu Met Ala Arg Glu Asn Gln
            755                 760                 765

Thr Thr Gly Tyr Gly Arg Asn Lys Ser Asn Gln Arg Leu Lys Arg Leu
770                 775                 780

Gln Asp Ser Leu Lys Glu Phe Gly Ser Asp Ile Leu Ser Lys Lys Lys
785                 790                 795                 800

Pro Ser Tyr Val Asp Ser Lys Val Glu Asn Ser His Leu Gln Asn Asp
                805                 810                 815

Arg Leu Phe Leu Tyr Tyr Ile Gln Asn Gly Lys Asp Met Tyr Thr Gly
            820                 825                 830

Glu Glu Leu Asp Ile Asp Arg Leu Ser Asp Tyr Asp Ile Asp His Ile
            835                 840                 845

Ile Pro Gln Ala Phe Ile Lys Asp Asn Ser Ile Asp Asn Lys Val Leu
850                 855                 860

Thr Ser Ser Ala Lys Asn Arg Gly Lys Ser Asp Asp Val Pro Ser Ile
865                 870                 875                 880

Glu Ile Val Arg Asn Arg Ser Tyr Trp Tyr Lys Leu Tyr Lys Ser
                885                 890                 895

Gly Leu Ile Ser Lys Arg Lys Phe Asp Asn Leu Thr Lys Ala Glu Arg
            900                 905                 910

Gly Gly Leu Thr Glu Ala Asp Lys Ala Gly Phe Ile Lys Arg Gln Leu
            915                 920                 925

Val Glu Thr Arg Gln Ile Thr Lys His Val Ala Gln Ile Leu Asp Ala
            930                 935                 940

Arg Phe Asn Thr Lys Arg Asp Glu Asn Asp Lys Val Ile Arg Asp Val
945                 950                 955                 960

Lys Val Ile Thr Leu Lys Ser Asn Leu Val Ser Gln Phe Arg Lys Glu
                965                 970                 975

Phe Lys Phe Tyr Lys Val Arg Glu Ile Asn Asp Tyr His His Ala His
            980                 985                 990

Asp Ala Tyr Leu Asn Ala Val Val Gly Thr Ala Leu Leu Lys Lys Tyr
            995                 1000                1005

Pro Lys Leu Thr Pro Glu Phe Val Tyr Gly Glu Tyr Lys Lys Tyr
    1010            1015               1020

Asp Val Arg Lys Leu Ile Ala Lys Ser Glu Asp Tyr Ser Glu
    1025            1030               1035
```

Met Gly Lys Ala Thr Ala Lys Tyr Phe Phe Tyr Ser Asn Leu Met
    1040                1045                1050

Asn Phe Phe Lys Thr Glu Val Lys Tyr Ala Asp Gly Arg Val Phe
    1055                1060                1065

Glu Arg Pro Asp Ile Glu Thr Asn Ala Asp Gly Glu Val Val Trp
    1070                1075                1080

Asn Lys Gln Lys Asp Phe Asp Ile Val Arg Lys Val Leu Ser Tyr
    1085                1090                1095

Pro Gln Val Asn Ile Val Lys Lys Val Glu Ala Gln Thr Gly Gly
    1100                1105                1110

Phe Ser Lys Glu Ser Ile Leu Ser Lys Gly Asp Ser Asp Lys Leu
    1115                1120                1125

Ile Pro Arg Lys Thr Lys Lys Val Tyr Trp Asn Thr Lys Lys Tyr
    1130                1135                1140

Gly Gly Phe Asp Ser Pro Thr Val Ala Tyr Ser Val Leu Val Val
    1145                1150                1155

Ala Asp Ile Glu Lys Gly Lys Ala Lys Lys Leu Lys Thr Val Lys
    1160                1165                1170

Glu Leu Val Gly Ile Ser Ile Met Glu Arg Ser Phe Phe Glu Glu
    1175                1180                1185

Asn Pro Val Ser Phe Leu Glu Lys Lys Gly Tyr His Asn Val Gln
    1190                1195                1200

Glu Asp Lys Leu Ile Lys Leu Pro Lys Tyr Ser Leu Phe Glu Phe
    1205                1210                1215

Glu Gly Gly Arg Arg Arg Leu Leu Ala Ser Ala Thr Glu Leu Gln
    1220                1225                1230

Lys Gly Asn Glu Val Met Leu Pro Ala His Leu Val Glu Leu Leu
    1235                1240                1245

Tyr His Ala His Arg Ile Asp Ser Phe Asn Ser Thr Glu His Leu
    1250                1255                1260

Lys Tyr Val Ser Glu His Lys Lys Glu Phe Glu Lys Val Leu Ser
    1265                1270                1275

Cys Val Glu Asn Phe Ser Asn Leu Tyr Val Asp Val Glu Lys Asn
    1280                1285                1290

Leu Ser Lys Val Arg Ala Ala Ala Glu Ser Met Thr Asn Phe Ser
    1295                1300                1305

Leu Glu Glu Ile Ser Ala Ser Phe Ile Asn Leu Leu Thr Leu Thr
    1310                1315                1320

Ala Leu Gly Ala Pro Ala Asp Phe Asn Phe Leu Gly Glu Lys Ile
    1325                1330                1335

Pro Arg Lys Arg Tyr Thr Ser Thr Lys Glu Cys Leu Ser Ala Thr
    1340                1345                1350

Leu Ile His Gln Ser Val Thr Gly Leu Tyr Glu Thr Arg Ile Asp
    1355                1360                1365

Leu Ser Lys Leu Gly Glu Glu
    1370                1375

<210> SEQ ID NO 3
<211> LENGTH: 1367
<212> TYPE: PRT
<213> ORGANISM: Artificial Sequence
<220> FEATURE:
<223> OTHER INFORMATION: ENGINEERED NICKASE

<400> SEQUENCE: 3

```
Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
            35                  40                  45

Gly Ala Leu Leu Phe Asp Ser Gly Ile Thr Ala Glu Gly Arg Arg Leu
        50                  55                  60

Lys Arg Thr Ala Arg Arg Tyr Thr Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
            115                 120                 125

His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
            195                 200                 205

Glu Glu Ile Val Lys Asp Lys Ile Ser Lys Leu Glu Lys Lys Asp Arg
        210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Lys Lys Tyr Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
            290                 295                 300

Ile Leu Thr Val Thr Asp Asn Gly Thr Glu Thr Pro Leu Ser Ser Ala
305                 310                 315                 320

Met Ile Met Arg Tyr Lys Glu His Glu Glu Asp Leu Gly Leu Leu Lys
                325                 330                 335

Ala Tyr Ile Arg Asn Ile Ser Leu Lys Thr Tyr Asn Glu Val Phe Asn
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Lys Phe Glu
        370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
```

```
            420                 425                 430
Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Thr Val Tyr Asn Glu Leu Thr Lys Val Arg
        515                 520                 525

Phe Ile Ala Glu Gly Met Ser Asp Tyr Gln Phe Leu Asp Ser Lys Gln
    530                 535                 540

Lys Lys Asp Ile Val Arg Leu Tyr Phe Lys Gly Lys Arg Lys Val Lys
545                 550                 555                 560

Val Thr Asp Lys Asp Ile Ile Glu Tyr Leu His Ala Ile Asp Gly Tyr
                565                 570                 575

Asp Gly Ile Glu Leu Lys Gly Ile Glu Lys Gln Phe Asn Ser Ser Leu
            580                 585                 590

Ser Thr Tyr His Asp Leu Leu Asn Ile Ile Asn Asp Lys Glu Phe Leu
        595                 600                 605

Asp Asp Ser Ser Asn Glu Ala Ile Ile Glu Glu Ile Ile His Thr Leu
    610                 615                 620

Thr Ile Phe Glu Asp Arg Glu Met Ile Lys Gln Arg Leu Ser Lys Phe
625                 630                 635                 640

Glu Asn Ile Phe Asp Lys Ser Val Leu Lys Lys Leu Ser Arg Arg His
                645                 650                 655

Tyr Thr Gly Trp Gly Lys Leu Ser Ala Lys Leu Ile Asn Gly Ile Arg
            660                 665                 670

Asp Glu Lys Ser Gly Asn Thr Ile Leu Asp Tyr Leu Ile Asp Asp Gly
        675                 680                 685

Ile Ser Asn Arg Asn Phe Met Gln Leu Ile His Asp Asp Ala Leu Ser
    690                 695                 700

Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
                725                 730                 735

Lys Lys Gly Ile Leu Gln Ser Ile Lys Ile Val Asp Glu Leu Val Lys
            740                 745                 750

Val Met Gly Arg Lys Pro Glu Ser Ile Val Val Glu Met Ala Arg Glu
        755                 760                 765

Asn Gln Tyr Thr Asn Gln Gly Lys Ser Asn Ser Gln Gln Arg Leu Lys
    770                 775                 780

Arg Leu Glu Glu Ser Leu Glu Glu Leu Gly Ser Lys Ile Leu Lys Glu
785                 790                 795                 800

Asn Ile Pro Ala Lys Leu Ser Lys Ile Asp Asn Asn Ser Leu Gln Asn
                805                 810                 815

Asp Arg Leu Tyr Leu Tyr Tyr Leu Gln Asn Gly Lys Asp Met Tyr Thr
            820                 825                 830

Gly Asp Asp Leu Asp Ile Asp Arg Leu Ser Asn Tyr Asp Ile Asp Ala
        835                 840                 845
```

-continued

```
Ile Ile Pro Gln Ala Phe Leu Lys Asp Asn Ser Ile Asp Asn Lys Val
850                 855                 860
Leu Val Ser Ser Ala Ser Asn Arg Gly Lys Ser Asp Asp Val Pro Ser
865                 870                 875                 880
Leu Glu Val Val Lys Lys Arg Lys Thr Leu Trp Tyr Gln Leu Leu Lys
                885                 890                 895
Ser Lys Leu Ile Ser Gln Arg Lys Phe Asp Asn Leu Thr Lys Ala Glu
                900                 905                 910
Arg Gly Gly Leu Ser Pro Glu Asp Lys Ala Gly Phe Ile Gln Arg Gln
                915                 920                 925
Leu Val Glu Thr Arg Gln Ile Thr Lys His Val Ala Arg Leu Leu Asp
930                 935                 940
Glu Lys Phe Asn Asn Lys Lys Asp Glu Asn Asn Arg Ala Val Arg Thr
945                 950                 955                 960
Val Lys Ile Ile Thr Leu Lys Ser Thr Leu Val Ser Gln Phe Arg Lys
                965                 970                 975
Asp Phe Glu Leu Tyr Lys Val Arg Glu Ile Asn Asp Phe His His Ala
                980                 985                 990
His Asp Ala Tyr Leu Asn Ala Val  Val Ala Ser Ala Leu  Leu Lys Lys
                995                 1000                1005
Tyr Pro Lys Leu Glu Pro Glu  Phe Val Tyr Gly Asp  Tyr Pro Lys
    1010                1015                1020
Tyr Asn Ser Phe Arg Glu Arg  Lys Ser Ala Thr Glu  Lys Val Tyr
    1025                1030                1035
Phe Tyr Ser Asn Ile Met Asn  Ile Phe Lys Lys Ser  Ile Ser Leu
    1040                1045                1050
Ala Asp Gly Arg Val Ile Glu  Arg Pro Leu Ile Glu  Val Asn Glu
    1055                1060                1065
Glu Thr Gly Glu Ser Val Trp  Asn Lys Glu Ser Asp  Leu Ala Thr
    1070                1075                1080
Val Arg Arg Val Leu Ser Tyr  Pro Gln Val Asn Val  Val Lys Lys
    1085                1090                1095
Val Glu Val Gln Ser Gly Gly  Phe Ser Lys Glu Leu  Val Gln Pro
    1100                1105                1110
His Gly Asn Ser Asp Lys Leu  Ile Pro Arg Lys Thr  Lys Lys Met
    1115                1120                1125
Ile Trp Asp Thr Lys Lys Tyr  Gly Gly Phe Asp Ser  Pro Ile Val
    1130                1135                1140
Ala Tyr Ser Val Leu Val Met  Ala Glu Arg Glu Lys  Gly Lys Ser
    1145                1150                1155
Lys Lys Leu Lys Pro Val Lys  Glu Leu Val Arg Ile  Thr Ile Met
    1160                1165                1170
Glu Lys Glu Ser Phe Lys Glu  Asn Thr Ile Asp Phe  Leu Glu Arg
    1175                1180                1185
Arg Gly Leu Arg Asn Ile Gln  Asp Glu Asn Ile Ile  Leu Leu Pro
    1190                1195                1200
Lys Phe Ser Leu Phe Glu Leu  Glu Asn Gly Arg Arg  Arg Leu Leu
    1205                1210                1215
Ala Ser Ala Lys Glu Leu Gln  Lys Gly Asn Glu Phe  Ile Leu Pro
    1220                1225                1230
Asn Lys Leu Val Lys Leu Leu  Tyr His Ala Lys Asn  Ile His Asn
    1235                1240                1245
```

-continued

```
Thr Leu Glu Pro Glu His Leu Glu Tyr Val Glu Ser His Arg Ala
    1250                1255                1260

Asp Phe Gly Lys Ile Leu Asp Val Val Ser Val Phe Ser Glu Lys
    1265                1270                1275

Tyr Ile Leu Ala Glu Ala Lys Leu Glu Lys Ile Lys Glu Ile Tyr
    1280                1285                1290

Arg Lys Asn Met Asn Thr Glu Ile His Glu Met Ala Thr Ala Phe
    1295                1300                1305

Ile Asn Leu Leu Thr Phe Thr Ser Ile Gly Ala Pro Ala Thr Phe
    1310                1315                1320

Lys Phe Phe Gly His Asn Ile Glu Arg Lys Arg Tyr Ser Ser Val
    1325                1330                1335

Ala Glu Ile Leu Asn Ala Thr Leu Ile His Gln Ser Val Thr Gly
    1340                1345                1350

Leu Tyr Glu Thr Arg Ile Asp Leu Gly Lys Leu Gly Glu Asp
    1355                1360                1365

<210> SEQ ID NO 4
<211> LENGTH: 1367
<212> TYPE: PRT
<213> ORGANISM: Artificial Sequence
<220> FEATURE:
<223> OTHER INFORMATION: ENGINEERED NICKASE

<400> SEQUENCE: 4

Met Thr Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Ala Leu Leu Phe Asp Ser Gly Ile Thr Ala Glu Gly Arg Arg Leu
    50                  55                  60

Lys Arg Thr Ala Arg Arg Arg Tyr Thr Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240
```

Phe Leu Lys Leu Ile Val Gly Asn Gln Ala Asp Phe Lys Lys Tyr Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Tyr Ser Asp
        275                 280                 285

Val Phe Leu Lys Ala Lys Lys Leu Tyr Asp Ala Ile Leu Leu Ser Gly
        290                 295                 300

Ile Leu Thr Val Thr Asp Asn Gly Thr Glu Thr Pro Leu Ser Ser Ala
305                 310                 315                 320

Met Ile Met Arg Tyr Lys Glu His Glu Glu Asp Leu Gly Leu Leu Lys
                325                 330                 335

Ala Tyr Ile Arg Asn Ile Ser Leu Lys Thr Tyr Asn Glu Val Phe Asn
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Lys Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Thr Val Tyr Asn Glu Leu Thr Lys Val Arg
        515                 520                 525

Phe Ile Ala Glu Gly Met Ser Asp Tyr Gln Phe Leu Asp Ser Lys Gln
    530                 535                 540

Lys Lys Asp Ile Val Arg Leu Tyr Phe Lys Gly Lys Arg Lys Val Lys
545                 550                 555                 560

Val Thr Asp Lys Asp Ile Ile Glu Tyr Leu His Ala Ile Asp Gly Tyr
                565                 570                 575

Asp Gly Ile Glu Leu Lys Gly Ile Glu Lys Gln Phe Asn Ser Ser Leu
            580                 585                 590

Ser Thr Tyr His Asp Leu Leu Asn Ile Ile Asn Asp Lys Glu Phe Leu
        595                 600                 605

Asp Asp Ser Ser Asn Glu Ala Ile Ile Glu Glu Ile Ile His Thr Leu
    610                 615                 620

Thr Ile Phe Glu Asp Arg Glu Met Ile Lys Gln Arg Leu Ser Lys Phe
625                 630                 635                 640

Glu Asn Ile Phe Asp Lys Ser Val Leu Lys Lys Leu Ser Arg Arg His
                645                 650                 655

Tyr Thr Gly Trp Gly Lys Leu Ser Ala Lys Leu Ile Asn Gly Ile Arg

-continued

```
                660                 665                 670
Asp Glu Lys Ser Gly Asn Thr Ile Leu Asp Tyr Leu Ile Asp Asp Gly
            675                 680                 685

Ile Ser Asn Arg Asn Phe Met Gln Leu Ile His Asp Asp Ala Leu Ser
        690                 695                 700

Phe Lys Lys Lys Ile Gln Lys Ala Gln Ile Ile Gly Asp Lys Asp Lys
705                 710                 715                 720

Asp Asn Ile Lys Glu Val Val Lys Ser Leu Pro Gly Ser Pro Ala Ile
                725                 730                 735

Lys Lys Gly Ile Leu Gln Ser Ile Lys Ile Val Asp Glu Leu Val Lys
            740                 745                 750

Val Met Gly Arg Lys Pro Glu Ser Ile Val Val Glu Met Ala Arg Glu
        755                 760                 765

Asn Gln Tyr Thr Asn Gln Gly Lys Ser Asn Ser Gln Gln Arg Leu Lys
    770                 775                 780

Arg Leu Glu Glu Ser Leu Glu Glu Leu Gly Ser Lys Ile Leu Lys Glu
785                 790                 795                 800

Asn Ile Pro Ala Lys Leu Ser Lys Ile Asp Asn Ser Leu Gln Asn
                805                 810                 815

Asp Arg Leu Tyr Leu Tyr Tyr Leu Gln Asn Gly Lys Asp Met Tyr Thr
            820                 825                 830

Gly Asp Asp Leu Asp Ile Asp Arg Leu Ser Asn Tyr Asp Ile Asp His
        835                 840                 845

Ile Ile Pro Gln Ala Phe Leu Lys Asp Asn Ser Ile Asp Asn Lys Val
    850                 855                 860

Leu Val Ser Ser Ala Ser Ala Arg Gly Lys Ser Asp Asp Val Pro Ser
865                 870                 875                 880

Leu Glu Val Val Lys Lys Arg Lys Thr Leu Trp Tyr Gln Leu Leu Lys
                885                 890                 895

Ser Lys Leu Ile Ser Gln Arg Lys Phe Asp Asn Leu Thr Lys Ala Glu
            900                 905                 910

Arg Gly Gly Leu Ser Pro Glu Asp Lys Ala Gly Phe Ile Gln Arg Gln
        915                 920                 925

Leu Val Glu Thr Arg Gln Ile Thr Lys His Val Ala Arg Leu Leu Asp
    930                 935                 940

Glu Lys Phe Asn Asn Lys Lys Asp Glu Asn Asn Arg Ala Val Arg Thr
945                 950                 955                 960

Val Lys Ile Ile Thr Leu Lys Ser Thr Leu Val Ser Gln Phe Arg Lys
                965                 970                 975

Asp Phe Glu Leu Tyr Lys Val Arg Glu Ile Asn Asp Phe His His Ala
            980                 985                 990

His Asp Ala Tyr Leu Asn Ala Val Val Ala Ser Ala Leu Leu Lys Lys
        995                 1000                1005

Tyr Pro Lys Leu Glu Pro Glu Phe Val Tyr Gly Asp Tyr Pro Lys
    1010                1015                1020

Tyr Asn Ser Phe Arg Glu Arg Lys Ser Ala Thr Glu Lys Val Tyr
    1025                1030                1035

Phe Tyr Ser Asn Ile Met Asn Ile Phe Lys Ser Ile Ser Leu
    1040                1045                1050

Ala Asp Gly Arg Val Ile Glu Arg Pro Leu Ile Glu Val Asn Glu
    1055                1060                1065

Glu Thr Gly Glu Ser Val Trp Asn Lys Glu Ser Asp Leu Ala Thr
    1070                1075                1080
```

Val Arg Arg Val Leu Ser Tyr Pro Gln Val Asn Val Lys Lys
    1085                1090                1095

Val Glu Val Gln Ser Gly Gly Phe Ser Lys Glu Leu Val Gln Pro
    1100                1105                1110

His Gly Asn Ser Asp Lys Leu Ile Pro Arg Lys Thr Lys Lys Met
    1115                1120                1125

Ile Trp Asp Thr Lys Lys Tyr Gly Gly Phe Asp Ser Pro Ile Val
    1130                1135                1140

Ala Tyr Ser Val Leu Val Met Ala Glu Arg Glu Lys Gly Lys Ser
    1145                1150                1155

Lys Lys Leu Lys Pro Val Lys Glu Leu Val Arg Ile Thr Ile Met
    1160                1165                1170

Glu Lys Glu Ser Phe Lys Glu Asn Thr Ile Asp Phe Leu Glu Arg
    1175                1180                1185

Arg Gly Leu Arg Asn Ile Gln Asp Glu Asn Ile Ile Leu Leu Pro
    1190                1195                1200

Lys Phe Ser Leu Phe Glu Leu Glu Asn Gly Arg Arg Arg Leu Leu
    1205                1210                1215

Ala Ser Ala Lys Glu Leu Gln Lys Gly Asn Glu Phe Ile Leu Pro
    1220                1225                1230

Asn Lys Leu Val Lys Leu Leu Tyr His Ala Lys Asn Ile His Asn
    1235                1240                1245

Thr Leu Glu Pro Glu His Leu Glu Tyr Val Glu Ser His Arg Ala
    1250                1255                1260

Asp Phe Gly Lys Ile Leu Asp Val Val Ser Val Phe Ser Glu Lys
    1265                1270                1275

Tyr Ile Leu Ala Glu Ala Lys Leu Glu Lys Ile Lys Glu Ile Tyr
    1280                1285                1290

Arg Lys Asn Met Asn Thr Glu Ile His Glu Met Ala Thr Ala Phe
    1295                1300                1305

Ile Asn Leu Leu Thr Phe Thr Ser Ile Gly Ala Pro Ala Thr Phe
    1310                1315                1320

Lys Phe Phe Gly His Asn Ile Glu Arg Lys Arg Tyr Ser Ser Val
    1325                1330                1335

Ala Glu Ile Leu Asn Ala Thr Leu Ile His Gln Ser Val Thr Gly
    1340                1345                1350

Leu Tyr Glu Thr Arg Ile Asp Leu Gly Lys Leu Gly Glu Asp
    1355                1360                1365

<210> SEQ ID NO 5
<211> LENGTH: 1375
<212> TYPE: PRT
<213> ORGANISM: Artificial Sequence
<220> FEATURE:
<223> OTHER INFORMATION: ENGINEERED NICKASE

<400> SEQUENCE: 5

Met Lys Lys Pro Tyr Ser Ile Gly Leu Asp Ile Gly Thr Asn Ser
1               5                  10                  15

Gly Trp Ala Val Ile Thr Asp Asp Tyr Lys Val Pro Ala Lys Lys Met
                20                  25                  30

Lys Val Leu Gly Asn Thr Asp Lys Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

-continued

```
Lys Arg Thr Ala Arg Arg Tyr Thr Arg Arg Lys Asn Arg Leu Arg
 65                  70                  75                  80

Tyr Leu Gln Glu Ile Phe Ala Lys Glu Met Thr Lys Val Asp Glu Ser
                 85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
            115                 120                 125

His Gln Lys Phe Pro Thr Ile Tyr His Leu Arg Lys Tyr Leu Ala Asp
        130                 135                 140

Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
                165                 170                 175

Glu Asn Thr Asp Val Gln Lys Leu Phe Asn Val Phe Val Glu Thr Tyr
            180                 185                 190

Asp Lys Ile Val Asp Glu Ser His Leu Ser Glu Ile Glu Val Asp Ala
        195                 200                 205

Ser Ser Ile Leu Thr Glu Lys Val Ser Lys Ser Arg Arg Leu Glu Asn
210                 215                 220

Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
                245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
        275                 280                 285

Leu Phe Ile Ser Ala Lys Asn Leu Tyr Asp Ala Ile Leu Leu Ser Gly
    290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
                325                 330                 335

Glu Phe Ile Lys Ile Asn Lys Leu Lys Leu Tyr His Asp Ile Phe Lys
            340                 345                 350

Asp Lys Thr Lys Asn Gly Tyr Ala Gly Tyr Ile Asp Asn Gly Val Lys
        355                 360                 365

Gln Asp Glu Phe Tyr Lys Tyr Leu Lys Thr Ile Leu Thr Lys Ile Asp
    370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
                405                 410                 415

Gln Glu Met His Ser Ile Leu Arg Arg Gln Gly Glu Tyr Tyr Pro Phe
            420                 425                 430

Leu Lys Glu Asn Gln Ala Lys Ile Glu Lys Ile Leu Thr Phe Arg Ile
        435                 440                 445

Pro Tyr Tyr Val Gly Pro Leu Ala Arg Lys Asp Ser Arg Phe Ala Trp
    450                 455                 460

Ala Asn Tyr His Ser Asp Glu Pro Ile Thr Pro Trp Asn Phe Asp Glu
465                 470                 475                 480
```

```
Val Val Asp Lys Glu Lys Ser Ala Glu Lys Phe Ile Thr Arg Met Thr
                485                 490                 495

Leu Asn Asp Leu Tyr Leu Pro Glu Glu Lys Val Leu Pro Lys His Ser
            500                 505                 510

His Val Tyr Glu Thr Phe Thr Val Tyr Asn Glu Leu Thr Lys Ile Lys
        515                 520                 525

Tyr Val Asn Glu Gln Gly Glu Ser Phe Phe Asp Ala Asn Met Lys
    530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
                565                 570                 575

Asn Asp Leu Ile Gly Leu Asp Lys Asp Ser Lys Ser Phe Asn Ala Ser
            580                 585                 590

Leu Gly Thr Tyr His Asp Leu Lys Lys Ile Leu Asp Lys Ser Phe Leu
        595                 600                 605

Asp Asp Lys Thr Asn Glu Gln Ile Ile Glu Asp Ile Val Leu Thr Leu
    610                 615                 620

Thr Leu Phe Glu Asp Arg Asp Met Ile His Glu Arg Leu Gln Lys Tyr
625                 630                 635                 640

Ser Asp Phe Phe Thr Ser Gln Gln Leu Lys Lys Leu Glu Arg Arg His
                645                 650                 655

Tyr Thr Gly Trp Gly Arg Leu Ser Tyr Lys Leu Ile Asn Gly Ile Arg
            660                 665                 670

Asn Lys Glu Asn Asn Lys Thr Ile Leu Asp Phe Leu Ile Asp Asp Gly
        675                 680                 685

His Ala Asn Arg Asn Phe Met Gln Leu Ile Asn Asp Glu Ser Leu Ser
    690                 695                 700

Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
                725                 730                 735

Gly Ile Leu Gln Ser Val Lys Ile Val Asp Glu Leu Val Lys Val Met
            740                 745                 750

Gly Asp Asn Pro Asp Asn Ile Val Ile Glu Met Ala Arg Glu Asn Gln
        755                 760                 765

Thr Thr Gly Tyr Gly Arg Asn Lys Ser Asn Gln Arg Leu Lys Arg Leu
    770                 775                 780

Gln Asp Ser Leu Lys Glu Phe Gly Ser Asp Ile Leu Ser Lys Lys
785                 790                 795                 800

Pro Ser Tyr Val Asp Ser Lys Val Glu Asn Ser His Leu Gln Asn Asp
                805                 810                 815

Arg Leu Phe Leu Tyr Tyr Ile Gln Asn Gly Lys Asp Met Tyr Thr Gly
            820                 825                 830

Glu Glu Leu Asp Ile Asp Arg Leu Ser Asp Tyr Asp Ile Asp Ala Ile
        835                 840                 845

Ile Pro Gln Ala Phe Ile Lys Asp Asn Ser Ile Asp Asn Lys Val Leu
    850                 855                 860

Thr Ser Ser Ala Lys Asn Arg Gly Lys Ser Asp Asp Val Pro Ser Ile
865                 870                 875                 880

Glu Ile Val Arg Asn Arg Arg Ser Tyr Trp Tyr Lys Leu Tyr Lys Ser
                885                 890                 895

Gly Leu Ile Ser Lys Arg Lys Phe Asp Asn Leu Thr Lys Ala Glu Arg
```

```
                900             905             910
Gly Gly Leu Thr Glu Ala Asp Lys Ala Gly Phe Ile Lys Arg Gln Leu
            915             920             925
Val Glu Thr Arg Gln Ile Thr Lys His Val Ala Gln Ile Leu Asp Ala
            930             935             940
Arg Phe Asn Thr Lys Arg Asp Glu Asn Asp Lys Val Ile Arg Asp Val
945             950             955             960
Lys Val Ile Thr Leu Lys Ser Asn Leu Val Ser Gln Phe Arg Lys Glu
                965             970             975
Phe Lys Phe Tyr Lys Val Arg Glu Ile Asn Asp Tyr His His Ala His
            980             985             990
Asp Ala Tyr Leu Asn Ala Val Val Gly Thr Ala Leu Leu Lys Lys Tyr
            995             1000            1005
Pro Lys Leu Thr Pro Glu Phe Val Tyr Gly Glu Tyr Lys Lys Tyr
    1010            1015            1020
Asp Val Arg Lys Leu Ile Ala Lys Ser Ser Asp Tyr Ser Glu
    1025            1030            1035
Met Gly Lys Ala Thr Ala Lys Tyr Phe Phe Tyr Ser Asn Leu Met
    1040            1045            1050
Asn Phe Phe Lys Thr Glu Val Lys Tyr Ala Asp Gly Arg Val Phe
    1055            1060            1065
Glu Arg Pro Asp Ile Glu Thr Asn Ala Asp Gly Glu Val Val Trp
    1070            1075            1080
Asn Lys Gln Lys Asp Phe Asp Ile Val Arg Lys Val Leu Ser Tyr
    1085            1090            1095
Pro Gln Val Asn Ile Val Lys Lys Val Glu Ala Gln Thr Gly Gly
    1100            1105            1110
Phe Ser Lys Glu Ser Ile Leu Ser Lys Gly Asp Ser Asp Lys Leu
    1115            1120            1125
Ile Pro Arg Lys Thr Lys Lys Val Tyr Trp Asn Thr Lys Lys Tyr
    1130            1135            1140
Gly Gly Phe Asp Ser Pro Thr Val Ala Tyr Ser Val Leu Val Val
    1145            1150            1155
Ala Asp Ile Glu Lys Gly Lys Ala Lys Lys Leu Lys Thr Val Lys
    1160            1165            1170
Glu Leu Val Gly Ile Ser Ile Met Glu Arg Ser Phe Phe Glu Glu
    1175            1180            1185
Asn Pro Val Ser Phe Leu Glu Lys Lys Gly Tyr His Asn Val Gln
    1190            1195            1200
Glu Asp Lys Leu Ile Lys Leu Pro Lys Tyr Ser Leu Phe Glu Phe
    1205            1210            1215
Glu Gly Gly Arg Arg Arg Leu Leu Ala Ser Ala Thr Glu Leu Gln
    1220            1225            1230
Lys Gly Asn Glu Val Met Leu Pro Ala His Leu Val Glu Leu Leu
    1235            1240            1245
Tyr His Ala His Arg Ile Asp Ser Phe Asn Ser Thr Glu His Leu
    1250            1255            1260
Lys Tyr Val Ser Glu His Lys Lys Glu Phe Glu Lys Val Leu Ser
    1265            1270            1275
Cys Val Glu Asn Phe Ser Asn Leu Tyr Val Asp Val Glu Lys Asn
    1280            1285            1290
Leu Ser Lys Val Arg Ala Ala Ala Glu Ser Met Thr Asn Phe Ser
    1295            1300            1305
```

-continued

```
Leu Glu Glu Ile Ser Ala Ser Phe Ile Asn Leu Leu Thr Leu Thr
    1310                1315                1320

Ala Leu Gly Ala Pro Ala Asp Phe Asn Phe Leu Gly Glu Lys Ile
    1325                1330                1335

Pro Arg Lys Arg Tyr Thr Ser Thr Lys Glu Cys Leu Ser Ala Thr
    1340                1345                1350

Leu Ile His Gln Ser Val Thr Gly Leu Tyr Glu Thr Arg Ile Asp
    1355                1360                1365

Leu Ser Lys Leu Gly Glu Glu
    1370                1375

<210> SEQ ID NO 6
<211> LENGTH: 1375
<212> TYPE: PRT
<213> ORGANISM: Artificial Sequence
<220> FEATURE:
<223> OTHER INFORMATION: ENGINEERED NICKASE

<400> SEQUENCE: 6

Met Lys Lys Pro Tyr Ser Ile Gly Leu Asp Ile Gly Thr Asn Ser Val
1               5                   10                  15

Gly Trp Ala Val Ile Thr Asp Asp Tyr Lys Val Pro Ala Lys Lys Met
            20                  25                  30

Lys Val Leu Gly Asn Thr Asp Lys Lys Tyr Ile Lys Lys Asn Leu Leu
        35                  40                  45

Gly Ala Leu Leu Phe Asp Ser Gly Glu Thr Ala Glu Val Thr Arg Leu
    50                  55                  60

Lys Arg Thr Ala Arg Arg Arg Tyr Thr Arg Arg Lys Asn Arg Leu Arg
65                  70                  75                  80

Tyr Leu Gln Glu Ile Phe Ala Lys Glu Met Thr Lys Val Asp Glu Ser
                85                  90                  95

Phe Phe Gln Arg Leu Glu Glu Ser Phe Leu Thr Asp Asp Lys Thr
            100                 105                 110

Phe Asp Ser His Pro Ile Phe Gly Asn Lys Ala Glu Glu Asp Ala Tyr
        115                 120                 125

His Gln Lys Phe Pro Thr Ile Tyr His Leu Arg Lys Tyr Leu Ala Asp
    130                 135                 140

Ser Gln Glu Lys Ala Asp Leu Arg Leu Val Tyr Leu Ala Leu Ala His
145                 150                 155                 160

Met Ile Lys Tyr Arg Gly His Phe Leu Ile Glu Gly Glu Leu Asn Ala
                165                 170                 175

Glu Asn Thr Asp Val Gln Lys Leu Phe Asn Val Phe Glu Thr Tyr
            180                 185                 190

Asp Lys Ile Val Asp Glu Ser His Leu Ser Glu Ile Glu Val Asp Ala
        195                 200                 205

Ser Ser Ile Leu Thr Glu Lys Val Ser Lys Ser Arg Arg Leu Glu Asn
    210                 215                 220

Leu Ile Lys Gln Tyr Pro Thr Glu Lys Lys Asn Thr Leu Phe Gly Asn
225                 230                 235                 240

Leu Ile Ala Leu Ala Leu Gly Leu Gln Pro Asn Phe Lys Thr Asn Phe
                245                 250                 255

Lys Leu Ser Glu Asp Ala Lys Leu Gln Phe Ser Lys Asp Thr Tyr Glu
            260                 265                 270

Glu Asp Leu Glu Glu Leu Leu Gly Lys Val Gly Asp Asp Tyr Ala Asp
        275                 280                 285
```

```
Leu Phe Ile Ser Ala Lys Asn Leu Tyr Asp Ala Ile Leu Ser Gly
            290                 295                 300

Ile Leu Thr Val Asp Asp Asn Ser Thr Lys Ala Pro Leu Ser Ala Ser
305                 310                 315                 320

Met Ile Lys Arg Tyr Val Glu His His Glu Asp Leu Glu Lys Leu Lys
                325                 330                 335

Glu Phe Ile Lys Ile Asn Lys Leu Lys Leu Tyr His Asp Ile Phe Lys
                340                 345                 350

Asp Lys Thr Lys Asn Gly Tyr Ala Gly Tyr Ile Asp Asn Gly Val Lys
            355                 360                 365

Gln Asp Glu Phe Tyr Lys Tyr Leu Lys Thr Ile Leu Thr Lys Ile Asp
370                 375                 380

Asp Ser Asp Tyr Phe Leu Asp Lys Ile Glu Arg Asp Asp Phe Leu Arg
385                 390                 395                 400

Lys Gln Arg Thr Phe Asp Asn Gly Ser Ile Pro His Gln Ile His Leu
                405                 410                 415

Gln Glu Met His Ser Ile Leu Arg Arg Gln Gly Glu Tyr Tyr Pro Phe
            420                 425                 430

Leu Lys Glu Asn Gln Ala Lys Ile Glu Lys Ile Leu Thr Phe Arg Ile
            435                 440                 445

Pro Tyr Tyr Val Gly Pro Leu Ala Arg Lys Asp Ser Arg Phe Ala Trp
            450                 455                 460

Ala Asn Tyr His Ser Asp Glu Pro Ile Thr Pro Trp Asn Phe Asp Glu
465                 470                 475                 480

Val Val Asp Lys Glu Lys Ser Ala Glu Lys Phe Ile Thr Arg Met Thr
                485                 490                 495

Leu Asn Asp Leu Tyr Leu Pro Glu Glu Lys Val Leu Pro Lys His Ser
            500                 505                 510

His Val Tyr Glu Thr Phe Thr Val Tyr Asn Glu Leu Thr Lys Ile Lys
            515                 520                 525

Tyr Val Asn Glu Gln Gly Glu Ser Phe Phe Phe Asp Ala Asn Met Lys
            530                 535                 540

Gln Glu Ile Phe Asp His Val Phe Lys Glu Asn Arg Lys Val Thr Lys
545                 550                 555                 560

Ala Lys Leu Leu Ser Tyr Leu Asn Asn Glu Phe Glu Glu Phe Arg Ile
                565                 570                 575

Asn Asp Leu Ile Gly Leu Asp Lys Asp Ser Lys Ser Phe Asn Ala Ser
            580                 585                 590

Leu Gly Thr Tyr His Asp Leu Lys Lys Ile Leu Asp Lys Ser Phe Leu
            595                 600                 605

Asp Asp Lys Thr Asn Glu Gln Ile Ile Glu Asp Ile Val Leu Thr Leu
610                 615                 620

Thr Leu Phe Glu Asp Arg Asp Met Ile His Glu Arg Leu Gln Lys Tyr
625                 630                 635                 640

Ser Asp Phe Phe Thr Ser Gln Gln Leu Lys Lys Leu Glu Arg Arg His
                645                 650                 655

Tyr Thr Gly Trp Gly Arg Leu Ser Tyr Lys Leu Ile Asn Gly Ile Arg
            660                 665                 670

Asn Lys Glu Asn Asn Lys Thr Ile Leu Asp Phe Leu Ile Asp Asp Gly
            675                 680                 685

His Ala Asn Arg Asn Phe Met Gln Leu Ile Asn Asp Glu Ser Leu Ser
            690                 695                 700
```

```
Phe Lys Thr Ile Ile Gln Glu Ala Gln Val Val Gly Asp Val Asp Asp
705                 710                 715                 720

Ile Glu Ala Val Val His Asp Leu Pro Gly Ser Pro Ala Ile Lys Lys
        725                 730                 735

Gly Ile Leu Gln Ser Val Lys Ile Val Asp Glu Leu Val Lys Val Met
            740                 745                 750

Gly Asp Asn Pro Asp Asn Ile Val Ile Glu Met Ala Arg Glu Asn Gln
                755                 760                 765

Thr Thr Gly Tyr Gly Arg Asn Lys Ser Asn Gln Arg Leu Lys Arg Leu
770                 775                 780

Gln Asp Ser Leu Lys Glu Phe Gly Ser Asp Ile Leu Ser Lys Lys Lys
785                 790                 795                 800

Pro Ser Tyr Val Asp Ser Lys Val Glu Asn Ser His Leu Gln Asn Asp
        805                 810                 815

Arg Leu Phe Leu Tyr Tyr Ile Gln Asn Gly Lys Asp Met Tyr Thr Gly
            820                 825                 830

Glu Glu Leu Asp Ile Asp Arg Leu Ser Asp Tyr Asp Ile Asp His Ile
                835                 840                 845

Ile Pro Gln Ala Phe Ile Lys Asp Asn Ser Ile Asp Asn Lys Val Leu
850                 855                 860

Thr Ser Ser Ala Lys Ala Arg Gly Lys Ser Asp Asp Val Pro Ser Ile
865                 870                 875                 880

Glu Ile Val Arg Asn Arg Arg Ser Tyr Trp Tyr Lys Leu Tyr Lys Ser
            885                 890                 895

Gly Leu Ile Ser Lys Arg Lys Phe Asp Asn Leu Thr Lys Ala Glu Arg
                900                 905                 910

Gly Gly Leu Thr Glu Ala Asp Lys Ala Gly Phe Ile Lys Arg Gln Leu
            915                 920                 925

Val Glu Thr Arg Gln Ile Thr Lys His Val Ala Gln Ile Leu Asp Ala
930                 935                 940

Arg Phe Asn Thr Lys Arg Asp Glu Asn Asp Lys Val Ile Arg Asp Val
945                 950                 955                 960

Lys Val Ile Thr Leu Lys Ser Asn Leu Val Ser Gln Phe Arg Lys Glu
            965                 970                 975

Phe Lys Phe Tyr Lys Val Arg Glu Ile Asn Asp Tyr His His Ala His
            980                 985                 990

Asp Ala Tyr Leu Asn Ala Val Val Gly Thr Ala Leu Leu Lys Lys Tyr
            995                 1000                1005

Pro Lys Leu Thr Pro Glu Phe Val Tyr Gly Glu Tyr Lys Lys Tyr
1010                1015                1020

Asp Val Arg Lys Leu Ile Ala Lys Ser Ser Asp Asp Tyr Ser Glu
1025                1030                1035

Met Gly Lys Ala Thr Ala Lys Tyr Phe Phe Tyr Ser Asn Leu Met
1040                1045                1050

Asn Phe Phe Lys Thr Glu Val Lys Tyr Ala Asp Gly Arg Val Phe
1055                1060                1065

Glu Arg Pro Asp Ile Glu Thr Asn Ala Asp Gly Glu Val Val Trp
1070                1075                1080

Asn Lys Gln Lys Asp Phe Asp Ile Val Arg Lys Val Leu Ser Tyr
1085                1090                1095

Pro Gln Val Asn Ile Val Lys Lys Val Glu Ala Gln Thr Gly Gly
1100                1105                1110

Phe Ser Lys Glu Ser Ile Leu Ser Lys Gly Asp Ser Asp Lys Leu
```

-continued

| | | | 1115 | | | | | 1120 | | | | 1125 | |
|---|---|---|---|---|---|---|---|---|---|---|---|---|---|

Ile Pro Arg Lys Thr Lys Val Tyr Trp Asn Thr Lys Lys Tyr
     1130                        1135                     1140

Gly Gly Phe Asp Ser Pro Thr Val Ala Tyr Ser Val Leu Val Val
   1145                     1150                    1155

Ala Asp Ile Glu Lys Gly Lys Ala Lys Lys Leu Lys Thr Val Lys
   1160                     1165                    1170

Glu Leu Val Gly Ile Ser Ile Met Glu Arg Ser Phe Phe Glu Glu
   1175                     1180                    1185

Asn Pro Val Ser Phe Leu Glu Lys Lys Gly Tyr His Asn Val Gln
   1190                     1195                    1200

Glu Asp Lys Leu Ile Lys Leu Pro Lys Tyr Ser Leu Phe Glu Phe
   1205                     1210                    1215

Glu Gly Gly Arg Arg Leu Leu Ala Ser Ala Thr Glu Leu Gln
   1220                     1225                    1230

Lys Gly Asn Glu Val Met Leu Pro Ala His Leu Val Glu Leu Leu
   1235                     1240                    1245

Tyr His Ala His Arg Ile Asp Ser Phe Asn Ser Thr Glu His Leu
   1250                     1255                    1260

Lys Tyr Val Ser Glu His Lys Lys Glu Phe Glu Lys Val Leu Ser
   1265                     1270                    1275

Cys Val Glu Asn Phe Ser Asn Leu Tyr Val Asp Val Glu Lys Asn
   1280                     1285                    1290

Leu Ser Lys Val Arg Ala Ala Ala Glu Ser Met Thr Asn Phe Ser
   1295                     1300                    1305

Leu Glu Glu Ile Ser Ala Ser Phe Ile Asn Leu Leu Thr Leu Thr
   1310                     1315                    1320

Ala Leu Gly Ala Pro Ala Asp Phe Asn Phe Leu Gly Glu Lys Ile
   1325                     1330                    1335

Pro Arg Lys Arg Tyr Thr Ser Thr Lys Glu Cys Leu Ser Ala Thr
   1340                     1345                    1350

Leu Ile His Gln Ser Val Thr Gly Leu Tyr Glu Thr Arg Ile Asp
   1355                     1360                    1365

Leu Ser Lys Leu Gly Glu Glu
   1370                     1375

<210> SEQ ID NO 7
<211> LENGTH: 36
<212> TYPE: DNA
<213> ORGANISM: Artificial Sequence
<220> FEATURE:
<223> OTHER INFORMATION: NATIVE CRISPR REPEAT

<400> SEQUENCE: 7
gttttagagc tgtgttgttt cgaatggttc caaaac          36

<210> SEQ ID NO 8
<211> LENGTH: 87
<212> TYPE: DNA
<213> ORGANISM: Artificial Sequence
<220> FEATURE:
<223> OTHER INFORMATION: NATIVE TRACR RNA

<400> SEQUENCE: 8
ggtttgaaac cattcgaaac aatacagcaa agttaaaata aggctagtcc gtatacaacg    60
tgaaaacacg tggcaccgat tcggtgc                                       87

<210> SEQ ID NO 9
<211> LENGTH: 123
<212> TYPE: DNA
<213> ORGANISM: Artificial Sequence
<220> FEATURE:
<223> OTHER INFORMATION: SGRNA2019V1

<400> SEQUENCE: 9
gttttagagc tgtgttgttt cgaatggttc caaaacggtt tgaaaccatt cgaaacaata    60
cagcaaagtt aaaataaggc tagtccgtat acaacgtgaa acacgtggc accgattcgg    120 tgc                                                                  123

<210> SEQ ID NO 10
<211> LENGTH: 91
<212> TYPE: DNA
<213> ORGANISM: Artificial Sequence
<220> FEATURE:
<223> OTHER INFORMATION: SGRNA2019V2

<400> SEQUENCE: 10
gttttagagc tgtgttgtaa aaacaataca gcaaagttaa aataaggcta gtccgtatac    60
aacgtgaaaa cacgtggcac cgattcggtg c                                   91

<210> SEQ ID NO 11
<211> LENGTH: 90
<212> TYPE: DNA
<213> ORGANISM: Artificial Sequence
<220> FEATURE:
<223> OTHER INFORMATION: SGRNA2019V3

<400> SEQUENCE: 11
gttttagagc tgtgttgtaa aaacaataca gcaagttaaa ataaggctag tccgtataca    60
acgtgaaaac acgtggcacc gattcggtgc                                     90

<210> SEQ ID NO 12
<211> LENGTH: 36
<212> TYPE: DNA
<213> ORGANISM: Artificial Sequence
<220> FEATURE:
<223> OTHER INFORMATION: NATIVE CRISPR REPEAT 2017

<400> SEQUENCE: 12
gttttagagc tgtgctgttt cgaatggttc caaaac                              36

<210> SEQ ID NO 13
<211> LENGTH: 87
<212> TYPE: DNA
<213> ORGANISM: Artificial Sequence
<220> FEATURE:
<223> OTHER INFORMATION: NATIVE TRACR RNA 2017

<400> SEQUENCE: 13
tgttggaact attcgaaaca acacagcgag ttaaataag gctttgtccg tacacaactt     60
gtaaaggggg cacccgattc gggtgca                                        87

<210> SEQ ID NO 14
<211> LENGTH: 101
<212> TYPE: DNA
<213> ORGANISM: Artificial Sequence
<220> FEATURE:
<223> OTHER INFORMATION: SGRNA2017V2

<400> SEQUENCE: 14

```
gttttagagc tgtgctgttt cgaaaaatcg aaacaacaca gcgagttaaa ataaggcttt    60
gtccgtacac aacttgtaaa aggggcaccc gattcgggtg c                       101

<210> SEQ ID NO 15
<211> LENGTH: 91
<212> TYPE: DNA
<213> ORGANISM: Artificial Sequence
<220> FEATURE:
<223> OTHER INFORMATION: SGRNA2017V3

<400> SEQUENCE: 15
gttttagagc tgtgctgtaa aaacaacaca gcgagttaaa ataaggcttt gtccgtacac    60
aacttgtaaa aggggcaccc gattcgggtg c                                  91

<210> SEQ ID NO 16
<211> LENGTH: 83
<212> TYPE: DNA
<213> ORGANISM: Artificial Sequence
<220> FEATURE:
<223> OTHER INFORMATION: SGRNA2017V4

<400> SEQUENCE: 16
gttttagagc tgtgcaaaca cagcgagtta aataaggct ttgtccgtac acaacttgta    60 aaagggcac ccgattcggg tgc                                            83

<210> SEQ ID NO 17
<211> LENGTH: 83
<212> TYPE: DNA
<213> ORGANISM: Artificial Sequence
<220> FEATURE:
<223> OTHER INFORMATION: SGRNA2019V2-1

<400> SEQUENCE: 17
gttttagagc tgtggaaata cagcaaagtt aaaataaggc tagtccgtat acaacgtgaa    60
aacacgtggc accgattcgg tgc                                           83

<210> SEQ ID NO 18
<211> LENGTH: 79
<212> TYPE: DNA
<213> ORGANISM: Artificial Sequence
<220> FEATURE:
<223> OTHER INFORMATION: SGRNA2019V2-2

<400> SEQUENCE: 18
gttttagagc tggaaacagc aaagttaaaa taaggctagt ccgtatacaa cgtgaaaaca    60
cgtggcaccg attcggtgc                                                79

<210> SEQ ID NO 19
<211> LENGTH: 79
<212> TYPE: DNA
<213> ORGANISM: Artificial Sequence
<220> FEATURE:
<223> OTHER INFORMATION: SGRNA2019V2-3

<400> SEQUENCE: 19
gtttaagagc tggaaacagc aaagtttaaa taaggctagt ccgtatacaa cgtgaaaaca    60
cgtggcaccg attcggtgc                                                79

<210> SEQ ID NO 20
<211> LENGTH: 79
<212> TYPE: DNA
```

```
<213> ORGANISM: Artificial Sequence
<220> FEATURE:
<223> OTHER INFORMATION: SGRNA2019V2-4

<400> SEQUENCE: 20
gttatagagc tggaaacagc aaagttataa taaggctagt ccgtatacaa cgtgaaaaca     60
cgtggcaccg attcggtgc                                                  79

<210> SEQ ID NO 21
<211> LENGTH: 79
<212> TYPE: DNA
<213> ORGANISM: Artificial Sequence
<220> FEATURE:
<223> OTHER INFORMATION: SGRNA2019V2-5

<400> SEQUENCE: 21
gtttaagagc tggaaacagc aaagtttaaa taaggctagt ccgtatacaa cgtggaaaca     60
cgtggcaccg attcggtgc                                                  79

<210> SEQ ID NO 22
<211> LENGTH: 79
<212> TYPE: DNA
<213> ORGANISM: Artificial Sequence
<220> FEATURE:
<223> OTHER INFORMATION: SGRNA2019V2-6

<400> SEQUENCE: 22
gttatagagc tggaaacagc aaagttataa taaggctagt ccgtatacaa cgtggaaaca     60
cgtggcaccg attcggtgc                                                  79

<210> SEQ ID NO 23
<211> LENGTH: 79
<212> TYPE: DNA
<213> ORGANISM: Artificial Sequence
<220> FEATURE:
<223> OTHER INFORMATION: SGRNA2019V2-7

<400> SEQUENCE: 23
gtttaagagc tggaaacagc aaagtttaaa taaggctagt ccgtatacaa cgtggaaaca     60
cgtggcaccg attcggtgc                                                  79

<210> SEQ ID NO 24
<211> LENGTH: 79
<212> TYPE: DNA
<213> ORGANISM: Artificial Sequence
<220> FEATURE:
<223> OTHER INFORMATION: SBRNA2019V2-8

<400> SEQUENCE: 24
gttatagagc tggaaacagc aaagttataa taaggctagt ccgtatacaa cgtggaaaca     60
cgtggcaccg attcggtgc                                                  79

<210> SEQ ID NO 25
<211> LENGTH: 79
<212> TYPE: DNA
<213> ORGANISM: Artificial Sequence
<220> FEATURE:
<223> OTHER INFORMATION: SGRNA2017V4-2

<400> SEQUENCE: 25
gtttaagagc tggaaacagc gagtttaaat aaggctttgt ccgtacacaa cttgtaaaag     60
gggcacccga ttcgggtgc                                                  79
```

<210> SEQ ID NO 26
<211> LENGTH: 79
<212> TYPE: DNA
<213> ORGANISM: Artificial Sequence
<220> FEATURE:
<223> OTHER INFORMATION: SGRNA2017V4-2-1

<400> SEQUENCE: 26
gtttaagagc tggaaacagc gagtttaaat aaggctttgt ccgtacacaa cttgtaaaag    60
gggcacccga ttcgggtgc                                                 79

<210> SEQ ID NO 27
<211> LENGTH: 79
<212> TYPE: DNA
<213> ORGANISM: Artificial Sequence
<220> FEATURE:
<223> OTHER INFORMATION: SGRNA2017V4-2-2

<400> SEQUENCE: 27
gtttaagagc tggaaacagc gagtttaaat aaggctttgt ccgtacacaa cttgaaaaag    60
gggcacccga ttcgggtgc                                                 79

<210> SEQ ID NO 28
<211> LENGTH: 20
<212> TYPE: DNA
<213> ORGANISM: Artificial Sequence
<220> FEATURE:
<223> OTHER INFORMATION: GUIDE

<400> SEQUENCE: 28
gctgaagcac tgcacgccgt                                                20

<210> SEQ ID NO 29
<211> LENGTH: 26
<212> TYPE: DNA
<213> ORGANISM: Artificial Sequence
<220> FEATURE:
<223> OTHER INFORMATION: HR IN CREATE FUSION

<400> SEQUENCE: 29
accctcagcc acggcgtgca gtgctt                                         26

<210> SEQ ID NO 30
<211> LENGTH: 17
<212> TYPE: DNA
<213> ORGANISM: Artificial Sequence
<220> FEATURE:
<223> OTHER INFORMATION: G4 SEQUENCE

<400> SEQUENCE: 30
actaacggtg gtggtgg                                                   17

<210> SEQ ID NO 31
<211> LENGTH: 20
<212> TYPE: DNA
<213> ORGANISM: Artificial Sequence
<220> FEATURE:
<223> OTHER INFORMATION: GUIDE

<400> SEQUENCE: 31
ggtgctgctt catgtggtcg                                                20

<210> SEQ ID NO 32

```
<211> LENGTH: 54
<212> TYPE: DNA
<213> ORGANISM: Artificial Sequence
<220> FEATURE:
<223> OTHER INFORMATION: HR IN CREATE FUSION

<400> SEQUENCE: 32
accctcagcc acggcgtgca gtgcttcagc cgctatcccg accacatgaa gcag          54
```

NUCLEIC ACID-GUIDED NICKASES

RELATED CASES

This application is a continuation of U.S. Ser. No. 17/463,581, filed 1 Sep. 2021, now allowed; which claims priority to U.S. Ser. No. 63/133,502, filed 4 Jan. 2021, which are incorporated herein in their entirety.

FIELD OF THE INVENTION

The present disclosure provides engineered nucleic acid-guided nickases and optimized scaffolds for making rational, direct edits to nucleic acids in live cells.

INCORPORATION BY REFERENCE

Submitted with the present application is an electronically filed sequence listing via EFS-Web as an ASCII formatted sequence listing, entitled "INSC094US_seq_list_20210818", created Aug. 18, 2021, and 77,000 bytes in size. The sequence listing is part of the specification filed herewith and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence; hence, gene function. These nucleases include nucleic acid-guided nucleases. The range of target sequences that nucleic acid-guided nucleases can recognize, however, is constrained by the need for a specific PAM to be located near the desired target sequence. Providing nucleases with altered PAM preferences and/or altered activity or fidelity may one goal of nuclease engineering. Another goal of engineering nucleic acid-guided nucleases may be to create nickases, which create single-strand breaks rather than double-stranded breaks. Such changes may increase the versatility of nucleic acid-guided nucleases for certain editing tasks.

There is thus a need in the art of nucleic acid-guided nuclease gene editing for novel nucleases or nickases with varied PAM preferences, varied activity in cells from different organisms, different cutting motifs and/or altered enzyme fidelity. The novel MAD nickases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Thus, the present disclosure embodies a nucleic acid-guided nickase selected from the following nickases: MAD2019-H848A, having the amino acid sequence of SEQ ID NO: 3; and MAD2019-N871A, having the amino acid sequence of SEQ ID NO: 4.

In some aspects, the MAD2019-H848A and MAD2019-N871A nickases are in a nucleic acid-guided nickase editing system with a gRNA scaffold having a nucleic acid sequence of SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; and in some aspects, the MAD2019-H848A and MAD2019-N871A nickases are in a nucleic acid-guided nickase editing system with a native CRISPR repeat having a nucleic acid sequence of SEQ ID NO: 7 and a native tracr RNA having a nucleic acid sequence of SEQ ID NO:8.

In yet other aspects, the MAD2019-H848A and MAD2019-N871A nickases are in a nucleic acid-guided nickase editing system comprising a guide RNA wherein the guide comprises from 5' to 3' a guide sequence, a homology region and SEQ ID NO: 30.

In addition, the present disclosure embodies a nucleic acid-guided nickase selected from the following nickases: MAD2017-H847A, having the amino acid sequence of SEQ ID NO: 5; and MAD2017-N870A, having the amino acid sequence of SEQ ID NO: 6.

In some aspects of this embodiment, the MAD2017-H847A and MAD2017-N870A nickases are in a nucleic acid-guided nickase editing system with a gRNA scaffold having a nucleic acid sequence of SEQ ID NO: 14, SEQ ID NO: 15, SEQ ID NO: 16, SEQ ID NO: 25, SEQ ID NO: 26, or SEQ ID NO: 27; and in some aspects, the MAD2017-H871A and MAD2017-N870A nickases are in a nucleic acid-guided nickase editing system with a native CRISPR repeat having a nucleic acid sequence of SEQ ID NO: 12 and a native tracr RNA having a nucleic acid sequence of SEQ ID NO:13.

In yet other aspects, the MAD2017-H847A and MAD2017-N870A nickases are in a nucleic acid-guided nickase editing system comprising a guide RNA wherein the guide comprises from 5' to 3' a guide sequence, a homology region and SEQ ID NO. 30.

These aspects and other features and advantages of the invention are described below in more detail.

BRIEF DESCRIPTION OF THE FIGURES

FIGS. 6A and 6B show the editing performance of CF MAD2017 nickase and various scaffolds with two CREATE Fusion (CF) guides.

Figure 1A:
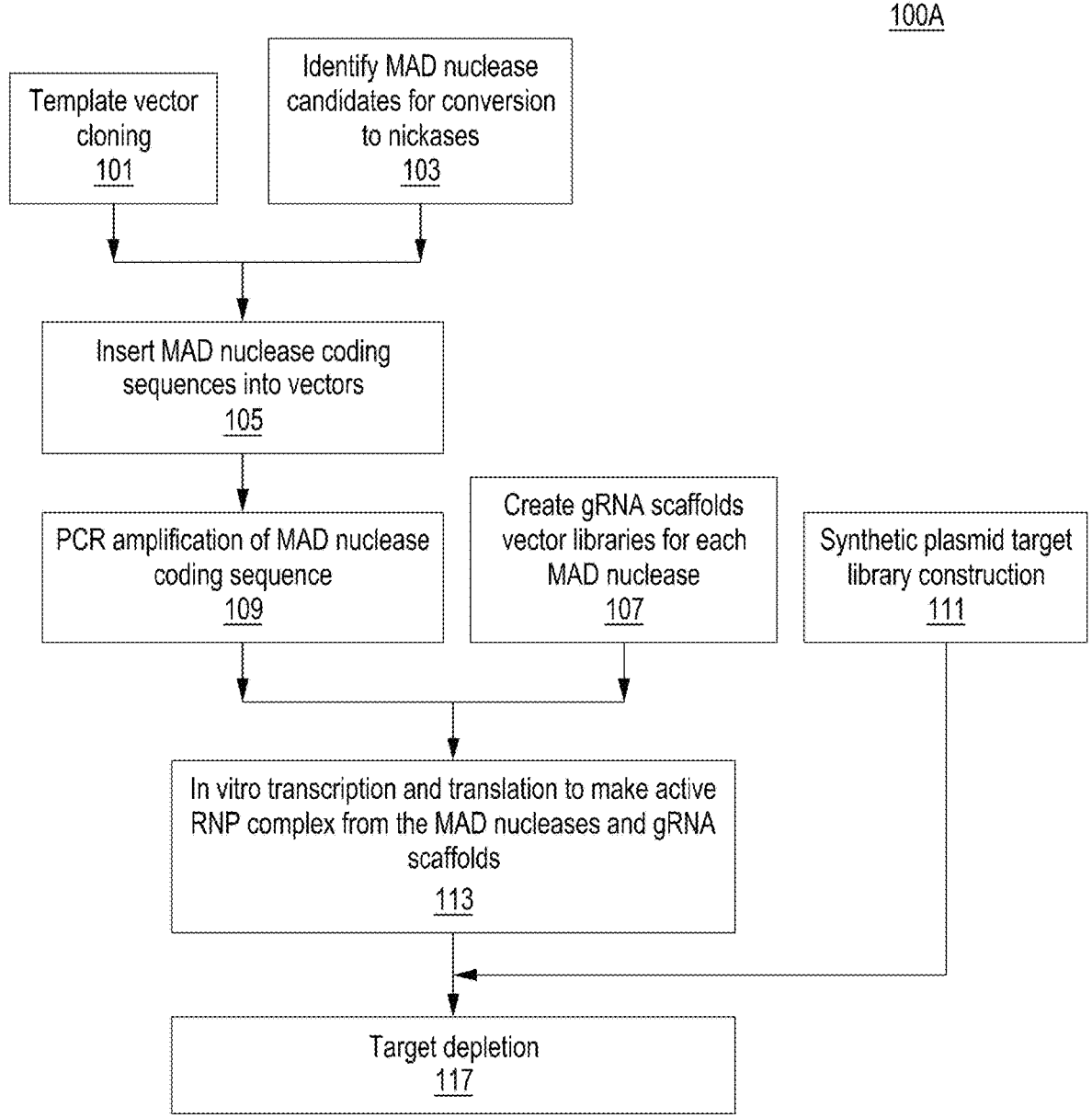
FIGS. 1A and 1B are exemplary workflows for screening for optimized scaffolds to be used with nucleic acid-guided nickases.

It should be understood that the drawings are not necessarily to scale.

DETAILED DESCRIPTION

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis and hybridization and ligation of polynucleotides. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), Lehninger, *Principles of Biochemistry* $3^{rd}$ Ed., W. H. Freeman Pub., New York, N.Y.; *Viral Vectors* (Kaplift & Loewy, eds., Academic Press 1995); all of which are herein incorporated in their entirety by reference for all purposes. For mammalian/stem cell culture and methods see, e.g., *Basic Cell Culture Protocols*, Fourth Ed. (Helgason & Miller, eds., Humana Press 2005); *Culture of Animal Cells*, Seventh Ed. (Freshney, ed., Humana Press 2016); *Microfluidic Cell Culture*, Second Ed. (Borenstein, Vandon, Tao & Charest, eds., Elsevier Press 2018); *Human Cell Culture* (Hughes, ed., Humana Press 2011); *3D Cell Culture* (Koledova, ed., Humana Press 2017); *Cell and Tissue Culture: Laboratory Procedures in Biotechnology* (Doyle & Griffiths, eds., John Wiley & Sons 1998); *Essential Stem Cell Methods*, (Lanza & Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza & Atala, eds., Academic Press 2013); and *Handbook of Stem Cells*, (Atala & Lanza, eds., Academic Press 2012). CRISPR-specific techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The terms "CREATE fusion enzyme" or the terms "nickase fusion" or "nickase fusion enzyme" refer to a nucleic acid-guided nickase fused to a reverse transcriptase where the fused enzyme both binds and nicks a target sequence in a sequence-specific manner and is capable of utilizing a repair template to incorporate nucleotides into the target sequence at the site of the nick.

The terms "editing cassette", "CREATE cassette", "CREATE editing cassette", "CREATE fusion editing cassette" or "CF editing cassette" refer to a nucleic acid molecule comprising a coding sequence for transcription of a guide nucleic acid or gRNA covalently linked to a coding sequence for transcription of a repair template.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the repair template with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refers to one, some, or all of a nucleic acid-guided nuclease or nickase fusion enzyme, a guide nucleic acid and a repair template.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible.

As used herein the terms "repair template" or "donor nucleic acid" or "donor DNA" or "homology arm" or "HA" or "homology region" or "HR" refer to 1) nucleic acid that is designed to introduce a DNA sequence modification (insertion, deletion, substitution) into a locus by homologous recombination using nucleic acid-guided nucleases, or 2) a nucleic acid that serves as a template (including a desired edit) to be incorporated into target DNA by a reverse transcriptase portion of a nickase fusion enzyme in a CREATE fusion (CF) editing system. For homology-directed repair, the repair template must have sufficient homology to the regions flanking the "cut site" or the site to be edited in the genomic target sequence. For template-directed repair, the repair template has homology to the genomic target sequence except at the position of the desired edit although synonymous edits may be present in the homologous (e.g., non-edit) regions. The length of the repair template(s) will depend on, e.g., the type and size of the modification being made. In many instances and preferably, the repair template will have two regions of sequence homology (e.g., two homology arms) complementary to the genomic target locus flanking the locus of the desired edit in the genomic target locus. Typically, an "edit region" or "edit locus" or "DNA sequence modification" region—the nucleic acid modification that one desires to be introduced into a genome target locus in a cell (e.g., the desired edit)—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "target genomic DNA sequence", "target sequence", or "genomic target locus" and the like refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The terms "transformation", "transfection" and "transduction" are used interchangeably herein to refer to the process of introducing exogenous DNA into cells.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. In some embodiments, a coding sequence for a nucleic acid-guided nuclease is provided in a vector, referred to as an "engine vector." In some embodiments, the editing cassette may be provided in a vector, referred to as an "editing vector." In some embodiments, the coding sequence for the nucleic acid-guided nuclease and the editing cassette are provided in the same vector.

Nucleic Acid-Guided Nuclease and Nickase Editing

The nucleic acid-guided nickases described herein are employed to allow one to perform nucleic acid nuclease-directed genome editing to introduce desired edits to a population of live mammalian cells. The nucleic acid-guided nickases described herein have been derived from nucleic acid-guided nucleases which were engineered to create a nick as opposed to a double-strand break. In addition to the nickases, gRNA scaffold (sgRNA) sequences have been identified to be used in a nucleic acid-guided nickase CF editing system with the engineered nickases to improve editing efficiency.

Generally, a nucleic acid-guided nuclease or nickase fusion enzyme complexed with an appropriate synthetic guide nucleic acid in a cell can cut the genome of the cell at a desired location. The guide nucleic acid helps the nucleic acid-guided nuclease or nickase fusion enzyme recognize and cut the DNA at a specific target sequence. By manipulating the nucleotide sequence of the guide nucleic acid, the nucleic acid-guided nuclease or nickase fusion enzyme may be programmed to target any DNA sequence for cleavage as long as an appropriate protospacer adjacent motif (PAM) is nearby. In certain aspects, the nucleic acid-guided nuclease system or nucleic acid-guided nickase fusion editing system (i.e., CF editing system) may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease or nickase fusion enzyme.

In general, a guide nucleic acid (e.g., gRNA) complexes with a compatible nucleic acid-guided nuclease or nickase fusion enzyme and can then hybridize with a target sequence, thereby directing the nuclease or nickase fusion to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. Preferably and typically, the guide nucleic acid comprises RNA and the gRNA is encoded by a DNA sequence on an editing cassette along with the coding sequence for a repair template. Covalently linking the gRNA and repair template allows one to scale up the number of edits that can be made in a population of cells tremendously. Methods and compositions for designing and synthesizing editing cassettes (e.g., CREATE cassettes) are described in U.S. Pat. Nos. 10,240,167; 10,266,849; 9,982,278; 10,351,877; 10,364,442; 10,435,715; 10,669,559; 10,711,284; 10,731,180, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease or nickase fusion enzyme to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease or gRNA/nickase fusion complex binds to a target sequence as determined by the guide RNA, and the nuclease or nickase fusion recognizes a protospacer adjacent motif (PAM) sequence adjacent to the target sequence. The target sequence can be any polynucleotide endogenous or exogenous to the cell, or in vitro. For example, in the case of mammalian cells the target sequence is typically a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA). The proto-spacer mutation (PAM) is a short nucleotide sequence recognized by the gRNA/nuclease complex. The precise preferred PAM sequence and length requirements for different nucleic acid-guided nucleases or nickase fusions vary; however, PAMs typically are 2-10 base-pair sequences adjacent or in proximity to the target sequence and, depending on the nuclease or nickase, can be 5' or 3' to the target sequence.

In most embodiments, genome editing of a cellular target sequence both introduces a desired DNA change (i.e., the desired edit) to a cellular target sequence, e.g., the genomic DNA of a cell, and removes, mutates, or renders inactive a proto-spacer/spacer mutation (PAM) region in the cellular target sequence (e.g., thereby rendering the target site immune to further nuclease binding). Rendering the PAM and/or spacer at the cellular target sequence inactive precludes additional editing of the cell genome at that cellular target sequence, e.g., upon subsequent exposure to a nucleic acid-guided nuclease or nickase fusion complexed with a synthetic guide nucleic acid in later rounds of editing. Thus, cells having the desired cellular target sequence edit and an altered PAM or spacer can be selected for by using a nucleic acid-guided nuclease or nickase fusion complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM or spacer alteration will not be cut, as these edited cells no longer contain the necessary PAM site and will continue to grow and propagate.

As for the nuclease or nickase fusion component of the nucleic acid-guided nuclease editing system, a polynucleotide sequence encoding the nucleic acid-guided nuclease or nickase fusion enzyme can be codon optimized for expression in particular cell types, such as bacterial, yeast, and, here, mammalian cells. The choice of the nucleic acid-guided nuclease or nickase fusion enzyme to be employed depends on many factors, such as what type of edit is to be made in the target sequence and whether an appropriate PAM is located close to the desired target sequence. Nucleic acid-guided nucleases (i.e., CRISPR enzymes) of use in the methods described herein include but are not limited to Cas 9, Cas 12/Cpf1, MAD2, or MAD7, MAD 2007 or other MADzymes and MADzyme systems (see U.S. Pat. Nos. 9,982,279; 10,337,028; 10,435,714; 10,011,849; 10,626,416; 10,604,746; 10,665,114; 10,640,754; 10,876,102; 10,883,077; 10,704,033; 10,745,678; 10,724,021; 10,767,169; and 10,870,761 for sequences and other details related to engineered and naturally-occurring MADzymes). Nickase fusion enzymes typically comprise a CRISPR nucleic acid-guided nuclease engineered to cut one DNA strand in a target DNA rather than making a double-stranded cut, and the nickase portion is fused to a reverse transcriptase. For more information on nickases and nickase fusion editing see U.S. Pat. No. 10,689,669 and Ser. Nos. 16/740,418; 16/740,420 and 16/740,421, all of which were filed 11 Jan. 2020. A coding sequence for a desired nuclease or nickase fusion may be on an "engine vector" along with other desired sequences such as a selective marker or may be transfected into a cell as a protein or ribonucleoprotein ("RNP") complex.

Another component of the nucleic acid-guided nuclease or nickase fusion system is the repair template comprising homology to the cellular target sequence. In some exemplary embodiments, the repair template is in the same editing cassette as (e.g., is covalently-linked to) the guide nucleic acid and typically is under the control of the same promoter as the gRNA (that is, a single promoter driving the transcription of both the editing gRNA and the repair template). The repair template is designed to serve as a template for homologous recombination with a cellular target sequence cleaved by a nucleic acid-guided nuclease or serve as the template for template-directed repair via a nickase fusion, as a part of the gRNA/nuclease complex. A repair template polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Pat. No. 10,711,284.

In certain preferred aspects, the repair template can be provided as an oligonucleotide of between 20-300 nucleotides, more preferably between 50-250 nucleotides. As described infra, the repair template comprises a region that is complementary to a portion of the cellular target sequence. When optimally aligned, the repair template overlaps with (is complementary to) the cellular target sequence by, e.g., about as few as 4 (in the case of nickase fusions) and as many as 20, 25, 30, 35, 40, 50, 60, 70, 80, 90 or more nucleotides (in the case of nucleases). The repair template comprises a region complementary to the cellular target sequence flanking the edit locus or difference between the repair template and the cellular target sequence. The desired edit may comprise an insertion, deletion, modification, or any combination thereof compared to the cellular target sequence.

As described in relation to the gRNA, the repair template may be provided as part of a rationally-designed editing cassette along with a promoter to drive transcription of both the gRNA and repair template. As described below, the editing cassette may be provided as a linear editing cassette, or the editing cassette may be inserted into an editing vector. Moreover, there may be more than one, e.g., two, three, four, or more editing gRNA/repair template pairs rationally-designed editing cassettes linked to one another in a linear "compound cassette" or inserted into an editing vector; alternatively, a single rationally-designed editing cassette may comprise two to several editing gRNA/repair template pairs, where each editing gRNA is under the control of separate different promoters, separate promoters, or where all gRNAs/repair template pairs are under the control of a single promoter. In some embodiments the promoter driving transcription of the editing gRNA and the repair template (or driving more than one editing gRNA/repair template pair) is an inducible promoter. In many if not most embodiments of the compositions, methods, modules and instruments described herein, the editing cassettes make up a collection or library editing of gRNAs and of repair templates representing, e.g., gene-wide or genome-wide libraries of editing gRNAs and repair templates.

In addition to the repair template, the editing cassettes comprise one or more primer binding sites to allow for PCR amplification of the editing cassettes. The primer binding sites are used to amplify the editing cassette by using oligonucleotide primers, and may be biotinylated or otherwise labeled. In addition, the editing cassette may comprise a barcode. A barcode is a unique DNA sequence that corresponds to the repair template sequence such that the barcode serves as a proxy to identify the edit made to the corresponding cellular target sequence. The barcode typically comprises four or more nucleotides. Also, in preferred embodiments, an editing cassette or editing vector or engine vector further comprises one or more nuclear localization sequences (NLSs), such as about or more than about 1, 2, 3, 4, 5, 6, 7, 8, 9, 10, or more NLSs.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 1B:
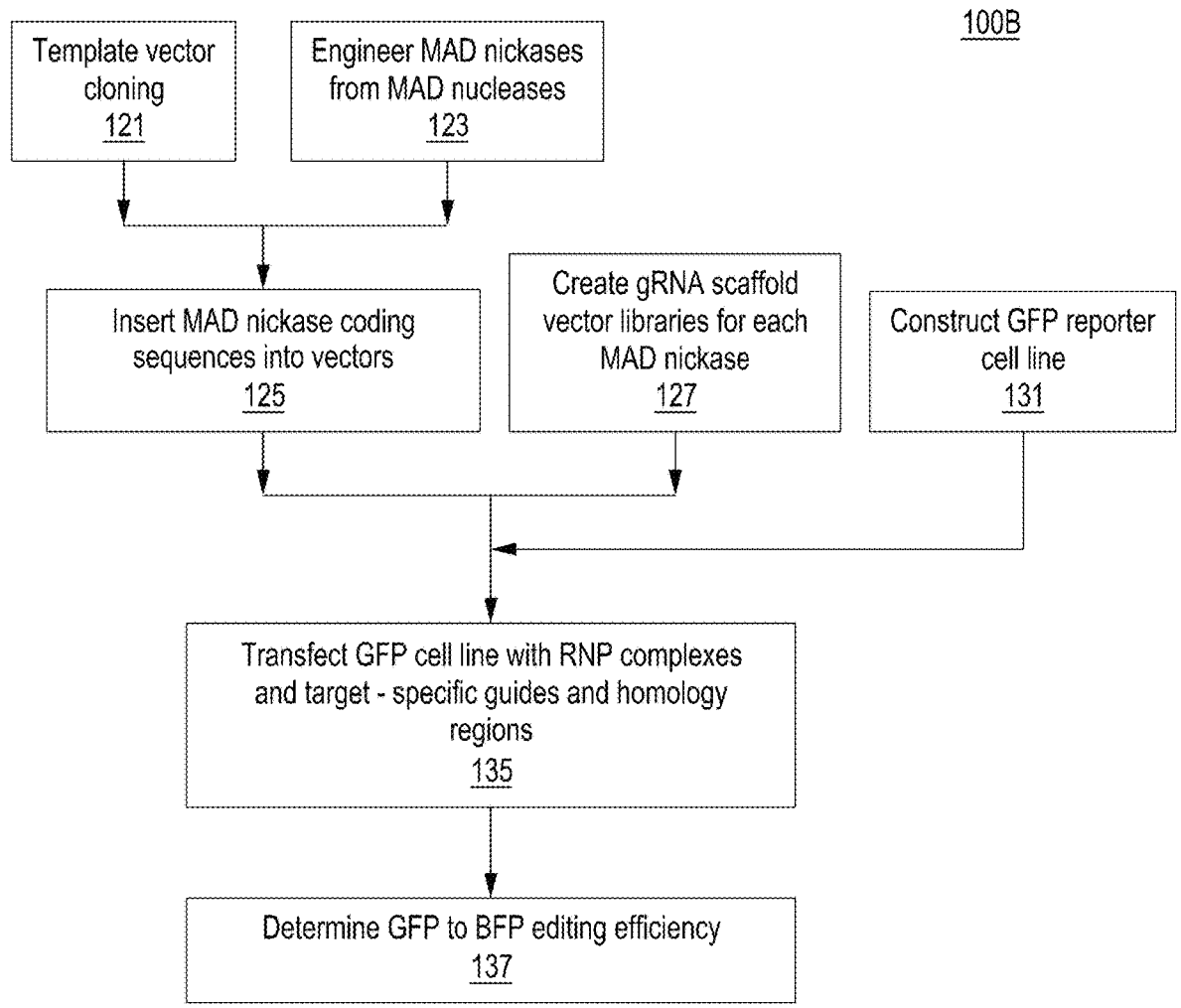

The disclosed MAD nucleic acid-guided nuclease and nickase fusion gRNA scaffolds were identified by the methods depicted in FIGS. 1A and 1B. The gRNA scaffolds form a part of a nucleic acid-guided nickase system for CF editing in cells. FIG. 1A shows an exemplary workflow 100A for screening MAD nucleic acid-guided nuclease and nickase scaffolds by determining cut activity using target depletion. In a first step 103, identified MAD nucleases identified as candidate for engineering. In parallel, a template vector is cloned 101. The coding sequences for the nucleic acid-guided nucleases are inserted into the template vector 105 and the nuclease sequences are amplified by PCR 109. Once the coding sequences for the nuclease are amplified 109, the native CRISPR repeat and tracrRNA for the nucleic acid-guided nuclease are used to construct variations on the gRNA scaffold structure 107 and are inserted into vector backbones. The nucleic acid-guided nucleases and sRNA scaffolds are transcribed, translated and combined to make active ribonucleoprotein (RNP) complexes 113. In parallel, synthetic targets were constructed 111 on which to test the RNP complexes for target depletion 117.

FIG. 1B shows an exemplary workflow 100B for screening of MAD nucleic acid-guided nickase scaffolds. In a first step 123, MAD nucleic acid-guided nucleases are identified as candidates for engineering nucleic acid-guided nickases. In parallel, a template vector is cloned 121. The coding sequences for the nucleic acid-guided nickases are inserted into the template vector 125 and the nuclease sequences are amplified by PCR. Once the coding sequences for the nickase are amplified, the native CRISPR repeat and tracrRNA for the nucleic acid-guided nuclease upon which the nickase is based are used to construct variations on the gRNA scaffold structure 127 and are inserted into vector backbones. The nucleic acid-guided nickases and gRNA scaffolds are transcribed, translated and combined to make active ribonucleoprotein (RNP) complexes. In parallel, a GFP reporter cell line is constructed 131. At step 135, the GFP reporter cell line is transfected with the RNP complexes and target-specific guides and homology regions. Finally, GFP to BFP editing efficiency 137 is determined.

Table 1 shows the amino acid sequences for the MAD2019 and MAD2017 nucleases on which the nickases are based (SEQ ID NO:1 and SEQ ID NO:2, respectively), as well as two nickases derived from each of these nucleases; namely, MAD2019-H848A (SEQ ID NO:3); MAD2019-N871A (SEQ ID NO:4); MAD2017-H847A (SEQ ID NO:5); and MAD2017-N870A (SEQ ID NO:6).

TABLE 1

| Sequence Description | Derived from | Amino Acid Sequence |
| --- | --- | --- |
| MAD2019 nuclease | *Streptococcus sp. (firmicutes)* | MTKPYSIGLDIGTNSVGWAVITDDYKVPSKKMKVLGNTSKKYIKKNLLGALLFDSGITAEGRRL KRTARRRYTRRRNRILYLQEIFSTEMATLDDAFFQRLDDSFLVPDDKRDSKYPIFGNLVEEKAY HDEFPTIYHLRKYLADSTKKADLRLVYLALAHMIKYRGHFLIEGEFNSKNNDIQKNFQDFLDTY NAIFESDLSLENSKQLEEIVKDKISKLEKKDRILKLFPGEKNSGIFSEFLKLIVGNQADFKKYFNLD EKASLHFSKESYDEDLETLLGYIGDDYSDVFLKAKKLYDAILLSGILTVTDNGTETPLSSAMIMRY KEHEEDLGLLKAYIRNISLKTYNEVFNDDTKNGYAGYIDGKTNQEDFYVYLKKLLAKFEGADYF LEKIDREDFLRKQRTFDNGSIPYQIHLQEMRAILDKQAKFYPFLAKNKERIEKILTFRIPYYVGPL ARGNSDFAWSIRKRNEKITPWNFEDVIDKESSAEAFINRMTSFDLYLPEEKVLPKHSLLYETFT VYNELTKVRFIAEGMSDYQFLDSKQKKDIVRLYFKGKRKVKVTDKDIIEYLHAIDGYDGIELKGI EKQFNSSLSTYHDLLNIINDKEFLDDSSNEAIIEEIIHTLTIFEDREMIKQRLSKFENIFDKSVLKKLS RRHYTGWGKLSAKLINGIRDEKSGNTILDYLIDDGISNRNFMQLIHDDALSFKKKIQKAQIIGD KDKDNIKEVVKSLPGSPAIKKGILQSIKIVDELVKVMGRKPESIVVEMARENQYTNQGKSNSQ QRLKRLEESLEELGSKILKENIPAKLSKIDNNSLQNDRLYLYYLQNGKDMYTGDDLDIDRLSNYD IDHIIPQAFLKDNSIDNKVLVSSASNRGKSDDVPSLEVVKKRKTLWYQLLKSKLISQRKFDNLTK AERGGLSPEDKAGFIQRQLVETRQITKHVARLLDEKFNNKKDENNRAVRTVKIITLKSTLVSQF RKDFELYKVREINDFHHAHDAYLNAVVASALLKKYPKLEPEFVYGDYPKYNSFRERKSATEKVY FYSNIMNIFKKSISLADGRVIERPLIEVNEETGESVWNKESDLATVRRVLSYPQVNVVKKVEVQ SGGFSKELVQPHGNSDKLIPRKTKKMIWDTKKYGGFDSPIVAYSVLVMAEREKGKSKKLKPVK ELVRITIMEKESFKENTIDFLERRGLRNIQDENIILLPKFSLFELENGRRRLLASAKELQKGNEFILP NKLVKLLYHAKNIHNTLEPEHLEYVESHRADFGKILDVVSVFSEKYILAEAKLEKIKEIYRKNMNT EIHEMATAFINLLTFTSIGAPATFKFFGHNIERKRYSSVAEILNATLIHQSVTGLYETRIDLGKLGE D [SEQ ID NO: 1] |
| MAD2017 nuclease | *Streptococcus sp. (firmicutes)* | MKKPYSIGLDIGTNSVGWAVITDDYKVPAKKMKVLGNTDKKYIKKNLLGALLFDSGETAEVTR LKRTARRRYTRRKNRLRYLQEIFAKEMTKVDESFFQRLEESFLTDDDKTFDSHPIFGNKAEEDA YHQKFPTIYHLRKYLADSQEKADLRLVYLALAHMIKYRGHFLIEGELNAENTDVQKLFNVFVET YDKIVDESHLSEIEVDASSILTEKVSKSRRLENLIKQYPTEKKNTLFGNLIALALGLQPNFKTNFKL SEDAKLQFSKDTYEEDLEELLGKVGDDYADLFISAKNLYDAILLSGILTVDDNSTKAPLSASMIK RYVEHHEDLEKLKEFIKINKLKLYHDIFKDKTKNGYAGYIDNGVKQDEFYKYLKTILTKIDDSDYF LDKIERDDFLRKQRTFDNGSIPHQIHLQEMHSILRRQGEYYPFLKENQAKIEKILTFRIPYYVGPL ARKDSRFAWANYHSDEPITPWNFDEVVDKEKSAEKFITRMTLNDLYLPEEKVLPKHSHVYETF TVYNELTKIKYVNEQGESFFFDANMKQEIFDHVFKENRKVTKAKLLSYLNNEFEEFRINDLIGL DKDSKSFNASLGTYHDLKKILDKSFLDDKTNEQIIEDIVLTLTLFEDRDMIHERLQKYSDFFTSQ QLKKLERRHYTGWGRLSYKLINGIRNKENNKTILDFLIDDGHANRNFMQLINDESLSFKTIIQE AQVVGDVDDIEAVVHDLPGSPAIKKGILQSVKIVDELVKVMGDNPDNIVIEMARENQTTGYG RNKSNQRLKRLQDSLKEFGSDILSKKKPSYVDSKVENSHLQNDRLFYYIQNGKDMYTGEELDI DRLSDYDIDHIIPQAFIKDNSIDNKVLTSSAKNRGKSDDVPSIEIVRNRRSYWYKLYKSGLISKRK FDNLTKAERGGLTEADKAGFIKRQLVETRQITKHVAQILDARFNTKRDENDKVIRDVKVITLKS NLVSQFRKEFKFYKVREINDYHHANDAYLNAVVGTALLKKYPKLTPEFVYGEYKKYDVRKLIAK SSDDYSEMGKATAKYFFYSNLMNFFKTEVKYADGRVFERPDIETNADGEVVWNKQKDFDIV RKVLSYPQVNIVKKVEAQTGGFSKESILSKGDSDKLIPRKTKKVYWNTKKYGGFDSPTVAYSVL VVADIEKGKAKKLKTVKELVGISIMERSFFEENPVSFLEKKGYHNVQEDKLIKLPKYSLFEFEGG RRRLLASATELQKGNEVMLPAHLVELLYHAHRIDSFNSTEHLKYVSEHKKEFEKVLSCVENFSN LYVDVEKNLSKVRAAAESMTNFSLEEISASFINLLTLTALGAPADFNFLGEKIPRKRYTSTKECLS ATLIHQSVTGLYETRIDLSKLGEE [SEQ ID NO: 2] |
| MAD2019 Nickase H848A | *Streptococcus sp. (firmicutes)* then engineered | MTKPYSIGLDIGTNSVGWAVITDDYKVPSKKMKVLGNTSKKYIKKNLLGALLFDSGITAEGRRL KRTARRRYTRRRNRILYLQEIFSTEMATLDDAFFQRLDDSFLVPDDKRDSKYPIFGNLVEEKAY HDEFPTIYHLRKYLADSTKKADLRLVYLALAHMIKYRGHFLIEGEFNSKNNDIQKNFQDFLDTY NAIFESDLSLENSKQLEEIVKDKISKLEKKDRILKLFPGEKNSGIFSEFLKLIVGNQADFKKYFNLD EKASLHFSKESYDEDLETLLGYIGDDYSDVFLKAKKLYDAILLSGILTVTDNGTETPLSSAMIMRY KEHEEDLGLLKAYIRNISLKTYNEVFNDDTKNGYAGYIDGKTNQEDFYVYLKKLLAKFEGADYF LEKIDREDFLRKQRTFDNGSIPYQIHLQEMRAILDKQAKFYPFLAKNKERIEKILTFRIPYYVGPL ARGNSDFAWSIRKRNEKITPWNFEDVIDKESSAEAFINRMTSFDLYLPEEKVLPKHSLLYETFT VYNELTKVRFIAEGMSDYQFLDSKQKKDIVRLYFKGKRKVKVTDKDIIEYLHAIDGYDGIELKGI EKQFNSSLSTYHDLLNIINDKEFLDDSSNEAIIEEIIHTLTIFEDREMIKQRLSKFENIFDKSVLKKLS RRHYTGWGKLSAKLINGIRDEKSGNTILDYLIDDGISNRNFMQLIHDDALSFKKKIQKAQIIGD KDKDNIKEVVKSLPGSPAIKKGILQSIKIVDELVKVMGRKPESIVVEMARENQYTNQGKSNSQ QRLKRLEESLEELGSKILKENIPAKLSKIDNNSLQNDRLYLYYLQNGKDMYTGDDLDIDRLSNYD IDAIIPQAFLKDNSIDNKVLVSSASNRGKSDDVPSLEVVKKRKTLWYQLLKSKLISQRKFDNLTK AERGGLSPEDKAGFIQRQLVETRQITKHVARLLDEKFNNKKDENNRAVRTVKIITLKSTLVSQF RKDFELYKVREINDFHHANDAYLNAVVASALLKKYPKLEPEFVYGDYPKYNSFRERKSATEKVY |

TABLE 1-continued

| Sequence Description | Derived from | Amino Acid Sequence |
|---|---|---|
| | | FYSNIMNIFKKSISLADGRVIERPLIEVNEETGESVWNKESDLATVRRVLSYPQVNVVKKVEVQ SGGFSKELVQPHGNSDKLIPRKTKKMIWDTKKYGGFDSPIVAYSVLVMAEREKGKSKKLKPVK ELVRITIMEKESFKENTIDFLERRGLRNIQDENIILLPKFSLFELENGRRRLLASAKELQKGNEFILP NKLVKLLYHAKNIHNTLEPEHLEYVESHRADFGKILDVVSVFSEKYILAEAKLEKIKEIYRKNMNT EIHEMATAFINLLTFTSIGAPATFKFFGHNIERKRYSSVAEILNATLIHQSVTGLYETRIDLGKLGE D<br>[SEQ ID NO: 3] |
| MAD2019 Nickase N871A | Streptococcus sp. (firmicutes) then engineered) | MTKPYSIGLDIGTNSVGWAVITDDYKVPSKKMKVLGNTSKKYIKKNLLGALLFDSGITAEGRRL KRTARRRYTRRRNRILYLQEIFSTEMATLDDAFFQRLDDSFLVPDDKRDSKYPIFGNLVEEKAY HDEFPTIYHLRKYLADSTKKADLRLVYLALAHMIKYRGHFLIEGEFNSKNNDIQKNFQDFLDTY NAIFESDLSLENSKQLEEIVKDKISKLEKKDRILKLFPGEKNSGIFSEFLKLIVGNQADFKKYFNLD EKASLHFSKESYDEDLETLLGYIGDDYSDVFLKAKKLYDAILLSGILTVTDNGTETPLSSAMIMRY KEHEEDLGLLKAYIRNISLKTYNEVFNDDTKNGYAGYIDGKTNQEDFYVYLKKLLAKFEGADYF LEKIDREDFLRKQRTFDNGSIPYQIHLQEMRAILDKQAKFYPFLAKNKERIEKILTFRIPYYVGPL ARGNSDFAWSIRKRNEKITPWNFEDVIDKESSAEAFINRMTSFDLYLPEEKVLPKHSLLYETFT VYNELTKVRFIAEGMSDYQFLDSKQKKDIVRLYFKGKRKVKVTDKDIIEYLHAIDGYDGIELKGI EKQFNSSLSTYHDLLNIINDKEFLDDSSNEAIIEEIIHTLTIFEDREMIKQRLSKFENIPDKSVLKKLS RRHYTGWGKLSAKLINGIRDEKSGNTILDYLIDDGISNRNFMQLIHDDALSFKKKIQKAQIIGD KDKDNIKEVVKSLPGSPAIKKGILQSIKIVDELVKVMGRKPESIVVEMARENQYTNQGKSNSQ QRLKRLEESLEELGSKILKENIPAKLSKIDNNSLQNDRLYLYYLQNGKDMYTGDDLDIDRLSNYD IDHIIPQAFLKDNSIDNKVLVSSASARGKSDDVPSLEVVKKRKTLWYQLLKSKLISQRKFDNLTK AERGGLSPEDKAGFIQRQLVETRQITKHVARLLDEKFNNKKDENNRAVRTVKIITLKSTLVSQF RKDFELYKVREINDFHHANDAYLNAVVASALLKKYPKLEPEFVYGDYPKYNSFRERKSATEKVY FYSNIMNIFKKSISLADGRVIERPLIEVNEETGESVWNKESDLATVRRVLSYPQVNVVKKVEVQ SGGFSKELVQPHGNSDKLIPRKTKKMIWDTKKYGGFDSPIVAYSVLVMAEREKGKSKKLKPVK ELVRITIMEKESFKENTIDFLERRGLRNIQDENIILLPKFSLFELENGRRRLLASAKELQKGNEFILP NKLVKLLYHAKNIHNTLEPEHLEYVESHRADFGKILDVVSVFSEKYILAEAKLEKIKEIYRKNMNT EIHEMATAFINLLTFTSIGAPATFKFFGHNIERKRYSSVAEILNATLIHQSVTGLYETRIDLGKLGE D<br>[SEQ ID NO: 4] |
| MAD2017 nickase H847A | Streptococcus sp. (firmicutes) then engineered) | MKKPYSIGLDIGTNSVGWAVITDDYKVPAKKMKVLGNTDKKYIKKNLLGALLFDSGETAEVTR LKRTARRRYTRRKNRLRYLQEIFAKEMTKVDESFFQRLEESFLTDDDKTFDSHPIFGNKAEEDA YHQKFPTIYHLRKYLADSQEKADLRLVYLALAHMIKYRGHFLIEGELNAENTDVQKLFNVFVET YDKIVDESHLSEIEVDASSILTEKVSKSRRLENLIKQYPTEKKNTLFGNLIALALGLQPNFKTNFKL SEDAKLQFSKDTYEEDLEELLGKVGDDYADLFISAKNLYDAILLSGILTVDDNSTKAPLSASMIK RYVEHHEDLEKLKEFIKINKLKLYHDIFKDKTKNGYAGYIDNGVKQDEFYKYLKTILTKIDDSDYF LDKIERDDFLRKQRTFDNGSIPHQIHLQEMHSILRRQGEYYPFLKENQAKIEKILTFRIPYYVGPL ARKDSRFAWANYHSDEPITPWNFDEVVDKEKSAEKFITRMTLNDLYLPEEKVLPKHSHVYETF TVYNELTKIKYVNEQGESFFFDANMKQEIFDHVFKENRKVTKAKLLSYLNNEFEEFRINDLIGL DKDSKSFNASLGTYHDLKKILDKSFLDDKTNEQIIEDIVLTLTLFEDRDMIHERLQKYSDFFTSQ QLKKLERRHYTGWGRLSYKLINGIRNKENNKTILDFLIDDGHANRNFMQLINDESLSFKTIIQE AQVVGDVDDIEAVVHDLPGSPAIKKGILQSVKIVDELVKVMGDNPDNIVIEMARENQTTGYG RNKSNQRLKRLQDSLKEFGSDILSKKKPSYVDSKVENSHLQNDRLFLYYIQNGKDMYTGEELDI DRLSDYDIDAIIPQAFIKDNSIDNKVLTSSAKNRGKSDDVPSIEIVRNNRSYWYKLYKSGLISKRK FDNLTKAERGGLTEADKAGFIKRQLVETRQITKHVAQILDARFNTKRDENDKVIRDVKVITLKS NLVSQFRKEFKFYKVREINDYHHAHDAYLNAVVGTALLKKYPKLTPEFVYGEYKKYDVRKLIAK SSDDYSEMGKATAKYFFYSNLMNFFKTEVKYADGRVFERPDIETNADGEVVWNKQKDFDIV RKVLSYPQVNIVKKVEAQTGGFSKESILKGDSDKLIPRKTKKVYWNTKKYGGFDSPTVAYSVL VVADIEKGKAKKLKTVKELVGISIMERSFFEENPVSFLEKKGYHNVQEDKLIKLPKYSLFEFEGG RRRLLASATELQKGNEVMLPAHLVELLYHAHRIDSFNSTEHLKYVSEHKKEFEKVLSCVENFSN LYVDVEKNLSKVRAAAESMTNFSLEEISASFINLLTLTALGAPADFNFLGEKIPRKRYTSTKECLS ATLIHQSVTGLYETRIDLSKLGEE<br>[SEQ ID NO: 5] |
| MAD2017 nickase N870A | Streptococcus sp. (firmicutes) then engineered | MKKPYSIGLDIGTNSVGWAVITDDYKVPAKKMKVLGNTDKKYIKKNLLGALLFDSGETAEVTR LKRTARRRYTRRKNRLRYLQEIFAKEMTKVDESFFQRLEESFLTDDDKTFDSHPIFGNKAEEDA YHQKFPTIYHLRKYLADSQEKADLRLVYLALAHMIKYRGHFLIEGELNAENTDVQKLFNVFVET YDKIVDESHLSEIEVDASSILTEKVSKSRRLENLIKQYPTEKKNTLFGNLIALALGLQPNFKTNFKL SEDAKLQFSKDTYEEDLEELLGKVGDDYADLFISAKNLYDAILLSGILTVDDNSTKAPLSASMIK RYVEHHEDLEKLKEFIKINKLKLYHDIFKDKTKNGYAGYIDNGVKQDEFYKYLKTILTKIDDSDYF LDKIERDDFLRKQRTFDNGSIPHQIHLQEMHSILRRQGEYYPFLKENQAKIEKILTFRIPYYVGPL ARKDSRFAWANYHSDEPITPWNFDEVVDKEKSAEKFITRMTLNDLYLPEEKVLPKHSHVYETF TVYNELTKIKYVNEQGESFFFDANMKQEIFDHVFKENRKVTKAKLLSYLNNEFEEFRINDLIGL DKDSKSFNASLGTYHDLKKILDKSFLDDKTNEQIIEDIVLTLTLFEDRDMIHERLQKYSDFFTSQ QLKKLERRHYTGWGRLSYKLINGIRNKENNKTILDFLIDDGHANRNFMQLINDESLSFKTIIQE AQVVGDVDDIEAVVHDLPGSPAIKKGILQSVKIVDELVKVMGDNPDNIVIEMARENQTTGYG RNKSNQRLKRLQDSLKEFGSDILSKKKPSYVDSKVENSHLQNDRLFLYYIQNGKDMYTGEELDI DRLSDYDIDHIIPQAFIKDNSIDNKVLTSSAKARGKSDDVPSIEIVRNRRSYWYKLYKSGLISKRK FDNLTKAERGGLTEADKAGFIKRQLVETRQITKHVAQILDARFNTKRDENDKVIRDVKVITLKS NLVSQFRKEFKFYKVREINDYHHAHDAYLNAVVGTALLKKYPKLTPEFVYGEYKKYDVRKLIAK SSDDYSEMGKATAKYFFYSNLMNFFKTEVKYADGRVFERPDIETNADGEVVWNKQKDFDIV |

TABLE 1-continued

| Sequence Description | Derived from | Amino Acid Sequence |
|---|---|---|
| | | RKVLSYPQVNIVKKVEAQTGGFSKESILSKGDSDKLIPRKTKKVYWNTKKYGGFDSPTVAYSVL<br>VVADIEKGKAKKLKTVKELVGISIMERSFFEENPVSFLEKKGYHNVQEDKLIKLPKYSLFEFEGG<br>RRRLLASATELQKGNEVMLPAHLVELLYHAHRIDSFNSTEHLKYVSEHKKEFEKVLSCVENFSN<br>LYVDVEKNLSKVRAAAESMTNFSLEEISASFINLLTLTALGAPADFNFLGEKIPRKRYTSTKECLS<br>ATLIHQSVTGLYETRIDLSKLGEE<br>[SEQ ID NO: 6] |

Example 2: Scaffold Optimization for the MAD2019 and MAD2017 Nickases

MAD2019 Nuclease: Three versions of gRNA scaffolds were designed using the MAD2019 nuclease native CRISPR repeat and tracr RNA sequences (corresponding to step 107 of FIG. 1A). The native CRISPR repeat and tracr RNA for the MAD2019 nuclease (SEQ ID NOs: 7 and 8, respectively), as well as the variant gRNA scaffolds (sgRNA) for MAD2019 (i.e., gRNA scaffold 2019v1 [SEQ ID NO:9]; gRNA scaffold 2019v2 [SEQ ID NO:10]; and gRNA scaffold 2019v3 [SEQ ID NO:11]) are shown in Table 2.

TABLE 2

First Round of Scaffold Optimization for MAD2019 Nickase

| Sequence Name | Sequence |
|---|---|
| Native CRISPR repeat MAD2019 | 5'-GTTTTAGAGCTGTGTTGTTTCGAATGGTTCCAAAAC-3'<br>[SEQ ID NO: 7] |
| Native tracr RNA MAD2019 | 5'-GGTTTGAAACCATTCGAAACAATACAGCAAAGTTAAAATAAGGCTA<br>GTCCGTATACAACGTGAAAACACGTGGCACCGATTCGGTGC-3'<br>[SEQ ID NO: 8] |
| sgRNA2019v1 | 5'-GTTTTAGAGCTGTGTTGTTTCGAATGGTTCCAAAACGGTTTGAAACCAT<br>TCGAAACAATACAGCAAAGTTAAAATAAGGCTAGTCCGTATACAACGTGA<br>AAACACGTGGCACCGATTCGGTGC-3'<br>[SEQ ID NO: 9] |
| sgRNA 2019v2 | 5'-GTTTTAGAGCTGTGTTGTAAAAACAATACAGCAAAGTTAAAATAAGGCT<br>AGTCCGTATACAACGTGAAAACACGTGGCACCGATTCGGTGC-3'<br>[SEQ ID NO: 10] |
| sgRNA 2019v3 | 5'-GTTTTAGAGCTGTGTTGTAAAAACAATACAGCAAGTTAAAATAAGGCTA<br>GTCCGTATACAACGTGAAAACACGTGGCACCGATTCGGTGC-3'<br>[SEQ ID NO: 11] |

Figure 2A:
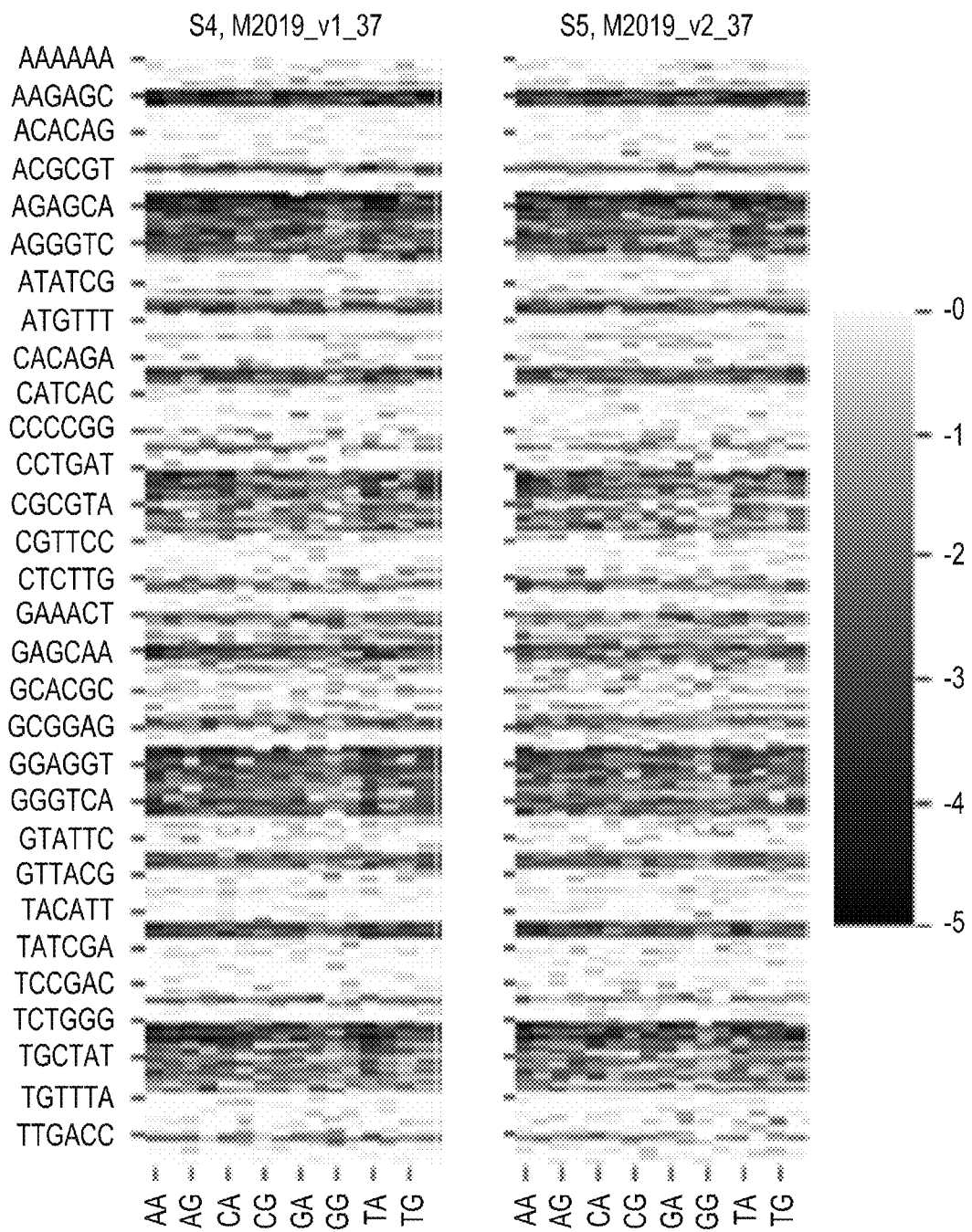
FIGS. 2A, 2B and 2C are heat maps showing the digestion patterns resulting from using the MAD2019 nuclease and three different guide RNAs with a plasmid target with degenerate PAM sequences at both 37° C. and 45° C.
Figure 2B:
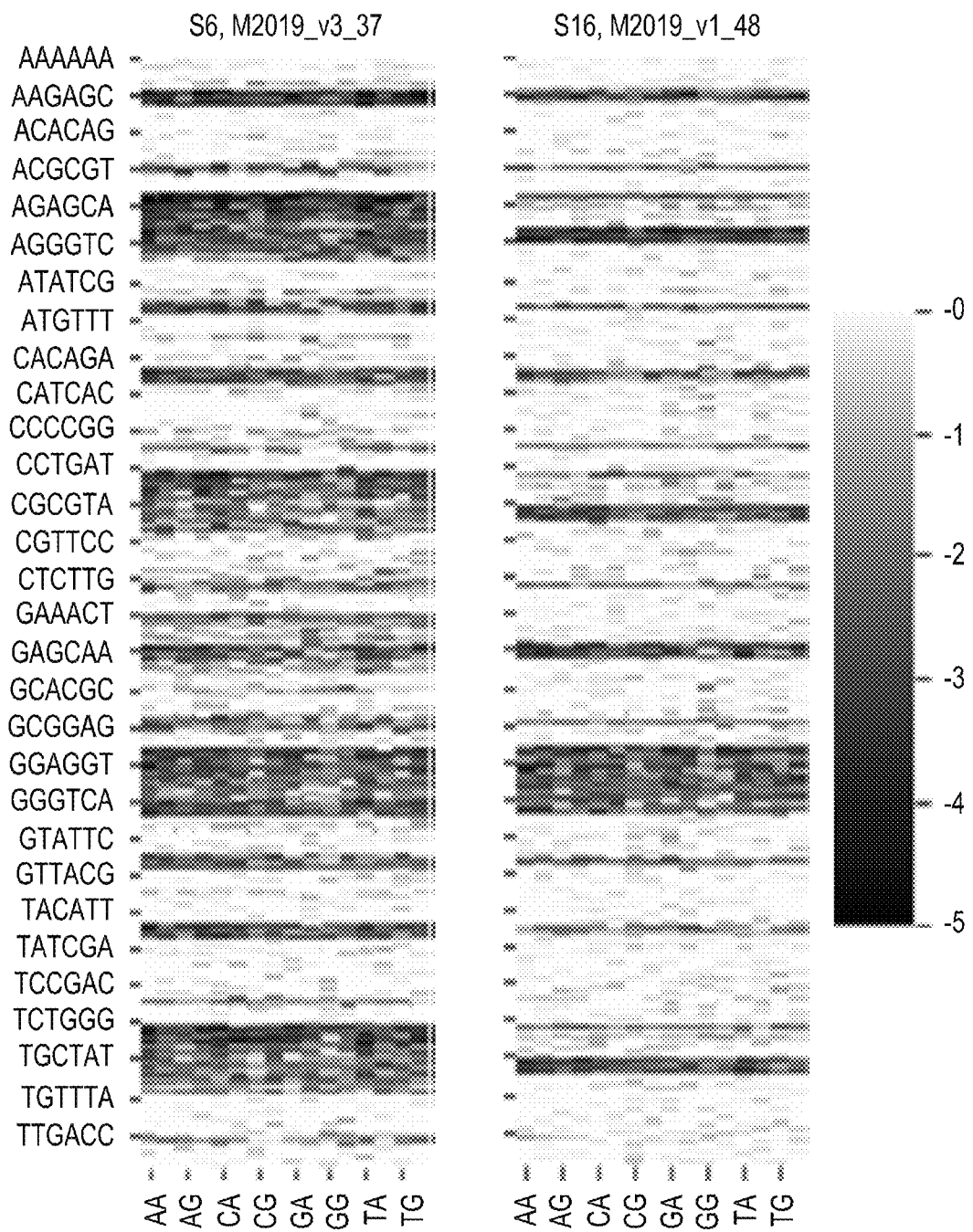
Figure 2C:
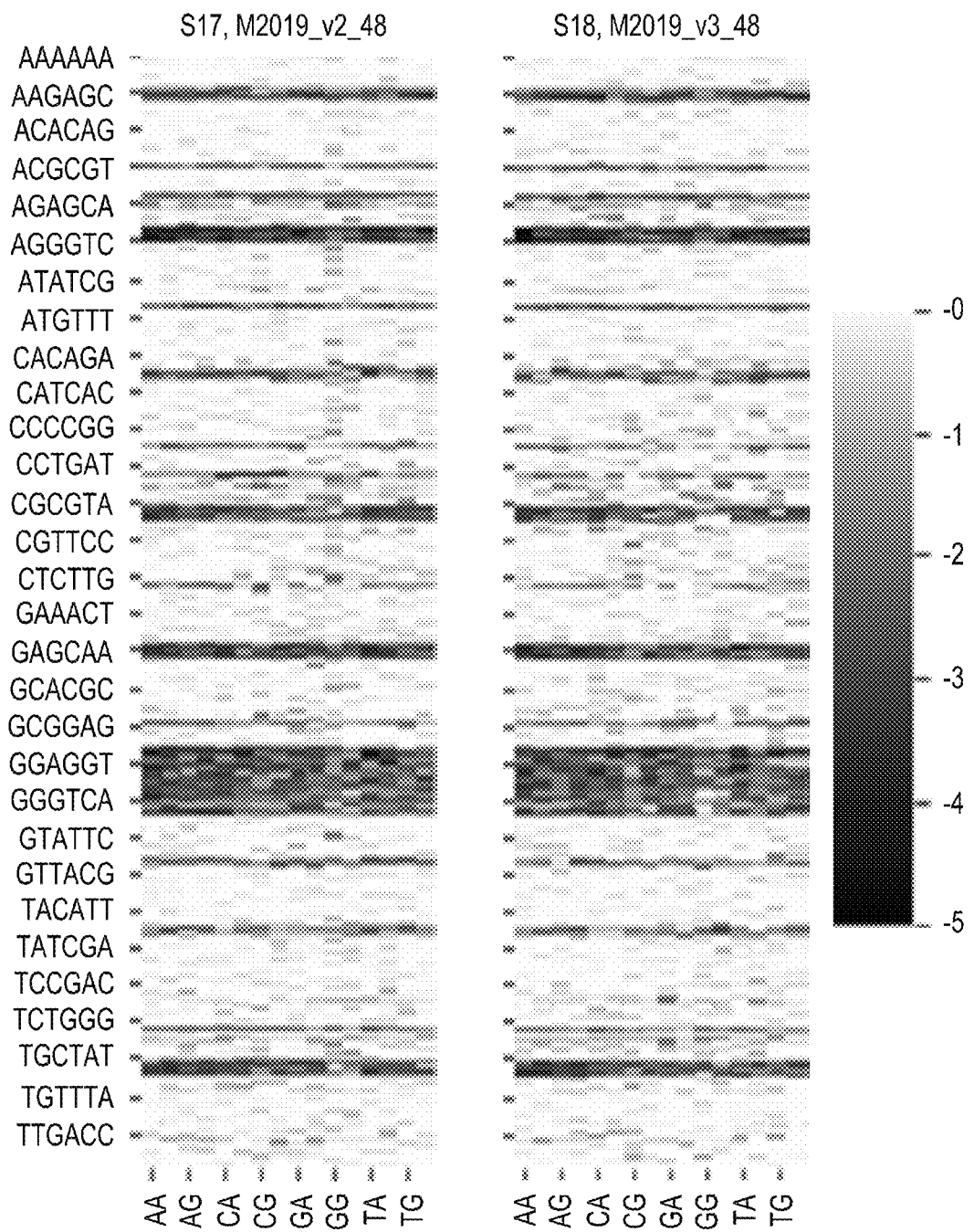

The MAD2019 nuclease and variant guide RNAs were produced in vitro to form RNP complexes (corresponding to step 113 of FIG. 1A) and the digestion patterns with a plasmid target, degenerate PAM sequences at two different temperatures (37° C. and 48° C.) were compared. The results are shown in FIGS. 2A-2C. There were no differences in performance in vitro between different variant sgRNAs used. An 8N degenerate PAM sequence was used in this assay. The Y-axis of FIGS. 2A-2C is for the first six nucleotides of the PAM and the two last nucleotides of the PAM are shown on the X-axis. A darker the color shows more depletion and higher activity.

MAD2017 Nuclease: Three versions of sgRNA scaffolds were designed using the MAD2017 nuclease native CRISPR repeat and tracr RNA sequences (corresponding to step 107 of FIG. 1A). The native CRISPR repeat and tracr RNA for the MAD2017 nuclease (SEQ ID NOs: 12 and 13, respectively), as well as the variant gRNA scaffolds for MAD2017 (i.e., gRNA scaffold2017v2 [SEQ ID NO:14]; gRNA scaffold2017v3 [SEQ ID NO:15]; and gRNA scaffold 2017v4 [SEQ ID NO:16]) are shown in Table 3.

TABLE 3

First Round of Scaffold Optimization for MAD2017 Nickase

| Sequence Name | Sequence |
|---|---|
| Native CRISPR repeat MAD2017 | 5'-GTTTTAGAGCTGTGCTGTTTCGAATGGTTCCAAAAC-3' [SEQ ID NO: 12] |
| Native tracr RNA MAD2017 | 5'-TGTTGGAACTATTCGAAACAACACAGCGAGTTAAAATAAGGCTTT GTCCGTACACAACTTGTAAAAGGGGCACCCGATTCGGGTGCA-3' [SEQ ID NO: 13] |
| sgRNA 2017v2 | 5'-GTTTTAGAGCTGTGCTGTTTCGAAAAATCGAAACAACACAGCGAGT TAAAATAAGGCTTTGTCCGTACACAACTTGTAAAAGGGGCACCCGATT CGGGTGC-3' [SEQ ID NO: 14] |
| sgRNA 2017v3 | 5'-GTTTTAGAGCTGTGCTGTAAAAACAACACAGCGAGTTAAAATAAGG CTTTGTCCGTACACAACTTGTAAAAGGGGCACCCGATTCGGGTGC-3' [SEQ ID NO: 15] |
| sgRNA 2017v4 | 5'-GTTTTAGAGCTGTGCAAACACAGCGAGTTAAAATAAGGCTTTGTCC GTACACAACTTGTAAAAGGGGCACCCGATTCGGGTGC-3' [SEQ ID NO: 16] |

Figure 3A:
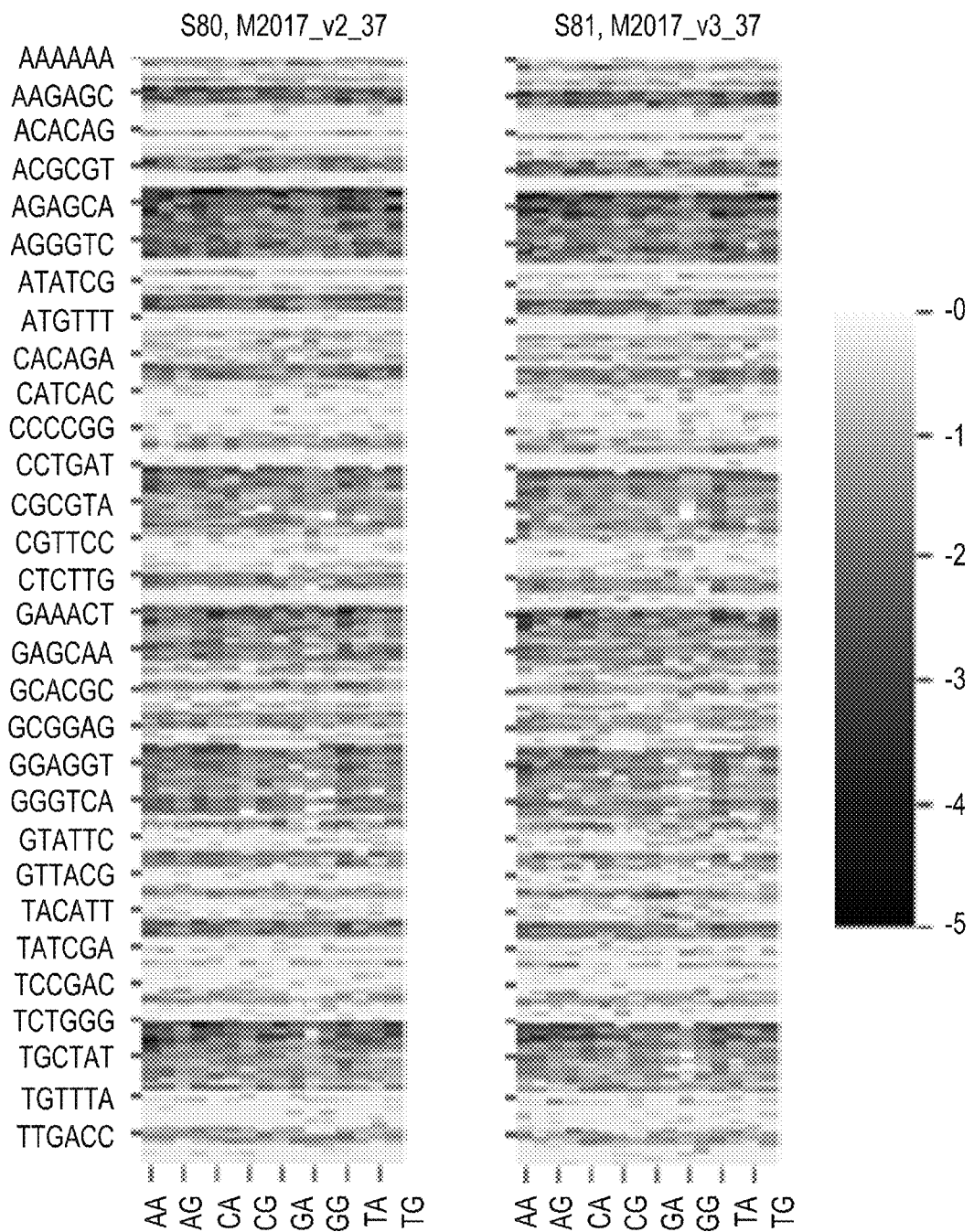
FIGS. 3A, 3B and 3C are heat maps showing the digestion pattern resulting from using the MAD2017 nuclease and three different guide RNAs with a plasmid target with degenerate PAM sequences at both 37° C. and 45° C.
Figure 3B:
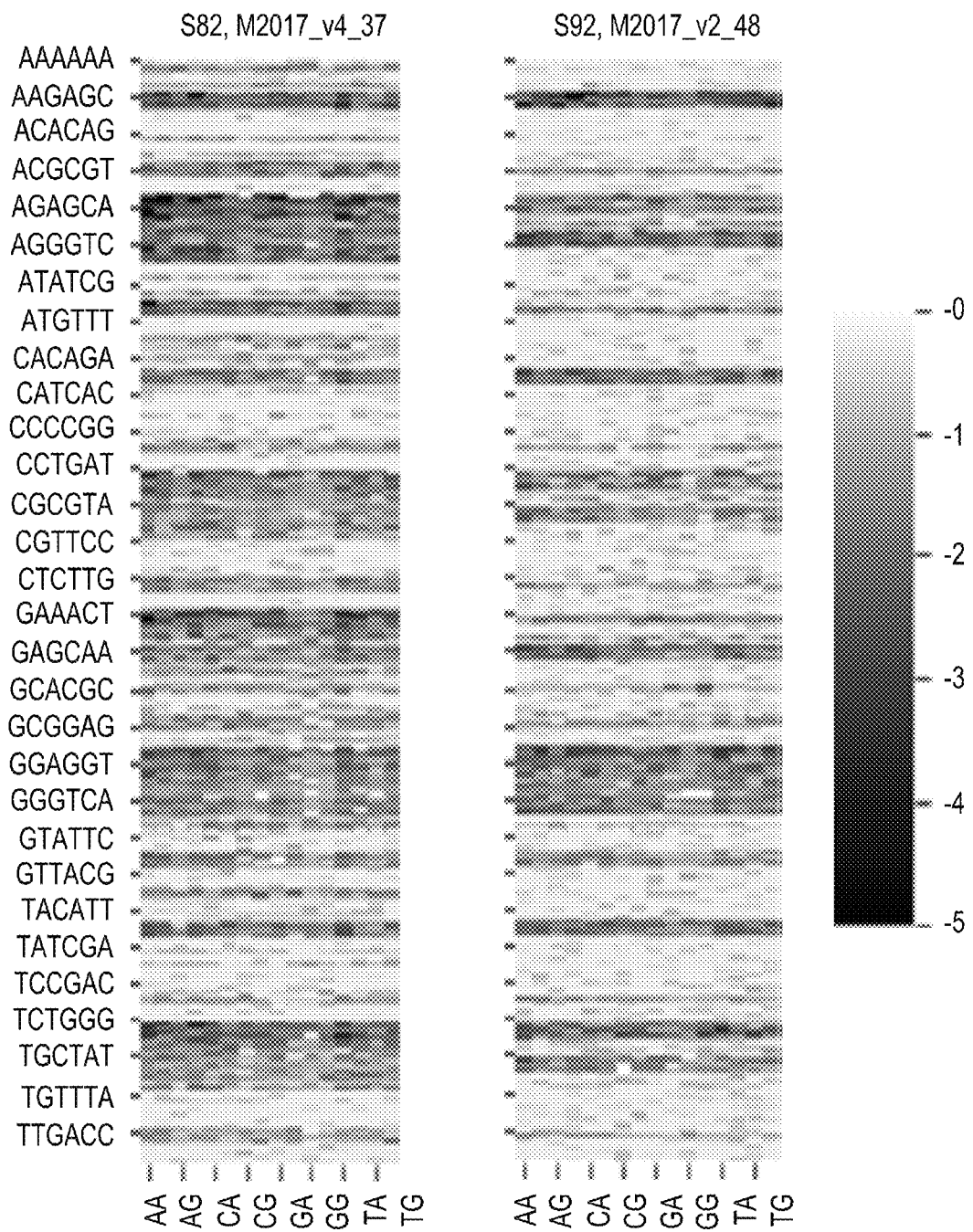
Figure 3C:
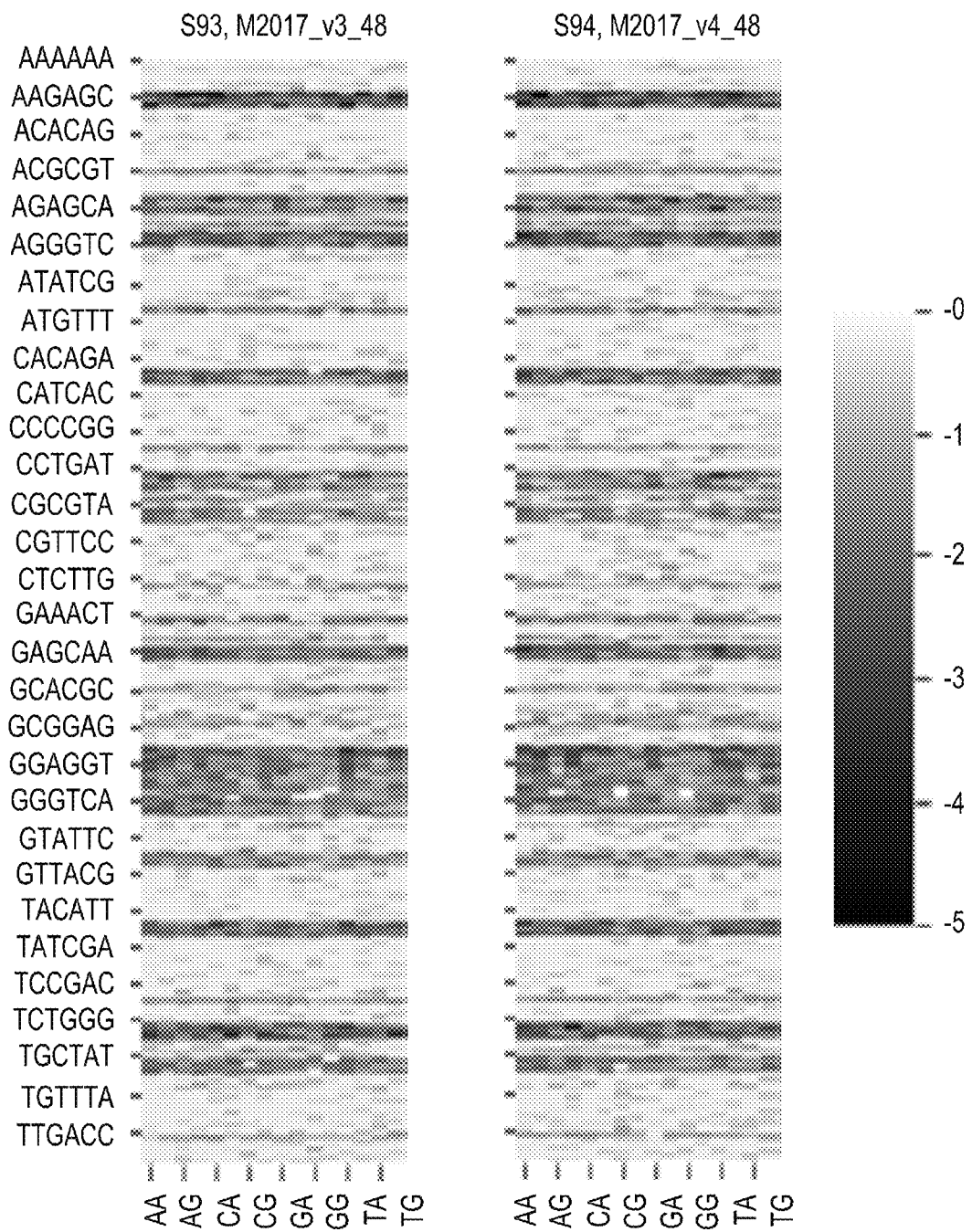

The MAD2017 nuclease and variant guide RNAs were produced in vitro to form RNP complexes (corresponding to step 113 of FIG. 1A) and the digestion patterns with a plasmid target, degenerate PAM sequences at two different temperatures (37° C. and 48° C.) were compared. The results are shown in FIGS. 3A-3C. There were no differences in performance in vitro between different variant sgRNAs used for the guide RNA production. An 8N degenerate PAM sequence was used in this assay. The Y-axis of FIGS. 3A-3C is for the first six nucleotides of the PAM and the two last nucleotides of the PAM are shown on the X-axis. A darker the color shows more depletion and higher activity.

Figure 4A:
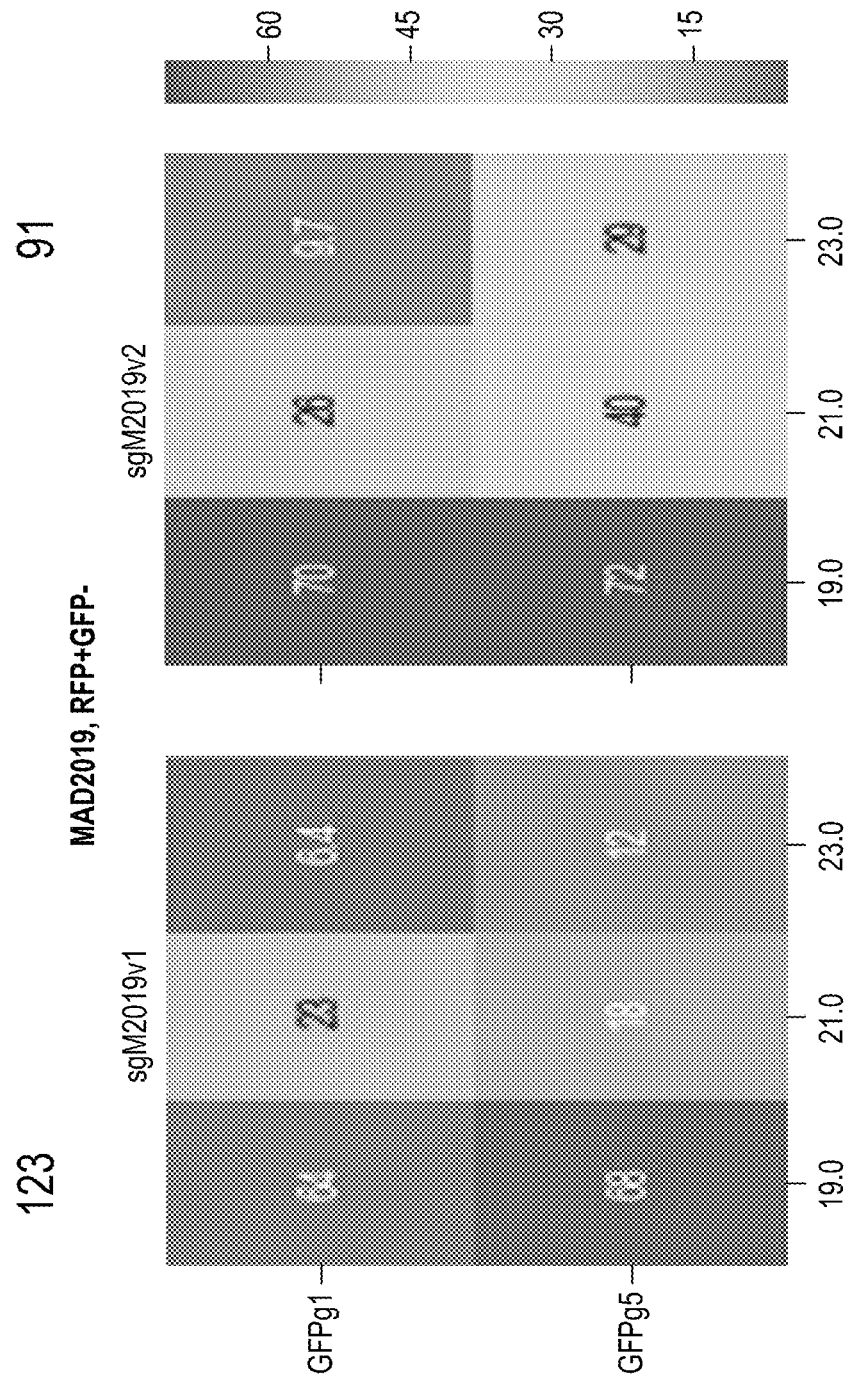
FIGS. 4A and 4B are heat maps showing the results where two sgRNA scaffolds for each of the MAD2019 and MAD107 nucleases were used to test double-strand break formation on a synthetic GFP locus integrated into HEK293T cells.
Figure 4B:
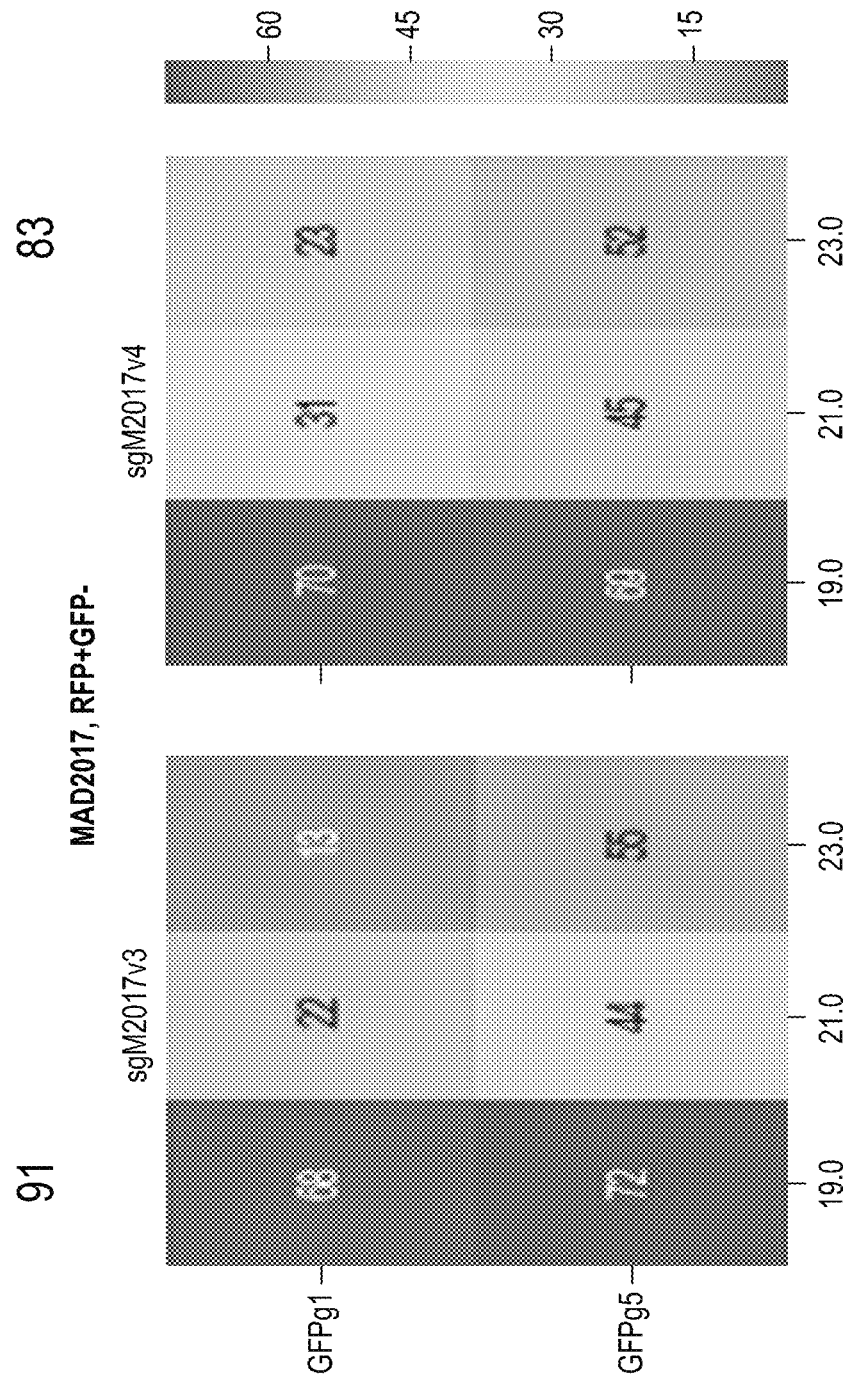

In vivo test of two scaffolds: A variant from the gRNA scaffolds listed in Tables 2 and 3 for each of MAD2019 and MAD2017 was used to test the effect on double strand break (DSB) formation activity on a GFP locus integrated in HEK293T cells. Three different guide lengths were tested (x-axis shown in FIGS. 4A and 4B), and two different guides (GFPg1 and GFPg5 in y-axis in FIGS. 4A and 4B) were used in different combinations. The sequences for GFPg1 and GFPg5 are shown in Table 4 below.

nuclease. Double-strand break activity was measured from the population of HEK293T cells that retained RFP signal after transfection and expanded for 5-6 days. The results are shown in FIGS. 4A and 4B. For both the MAD2019 and MAD2017 nucleases, the 19-bp guides were the most efficient; and with this optimal guide length, there were no differences in cutting activity.

Figure 5A:
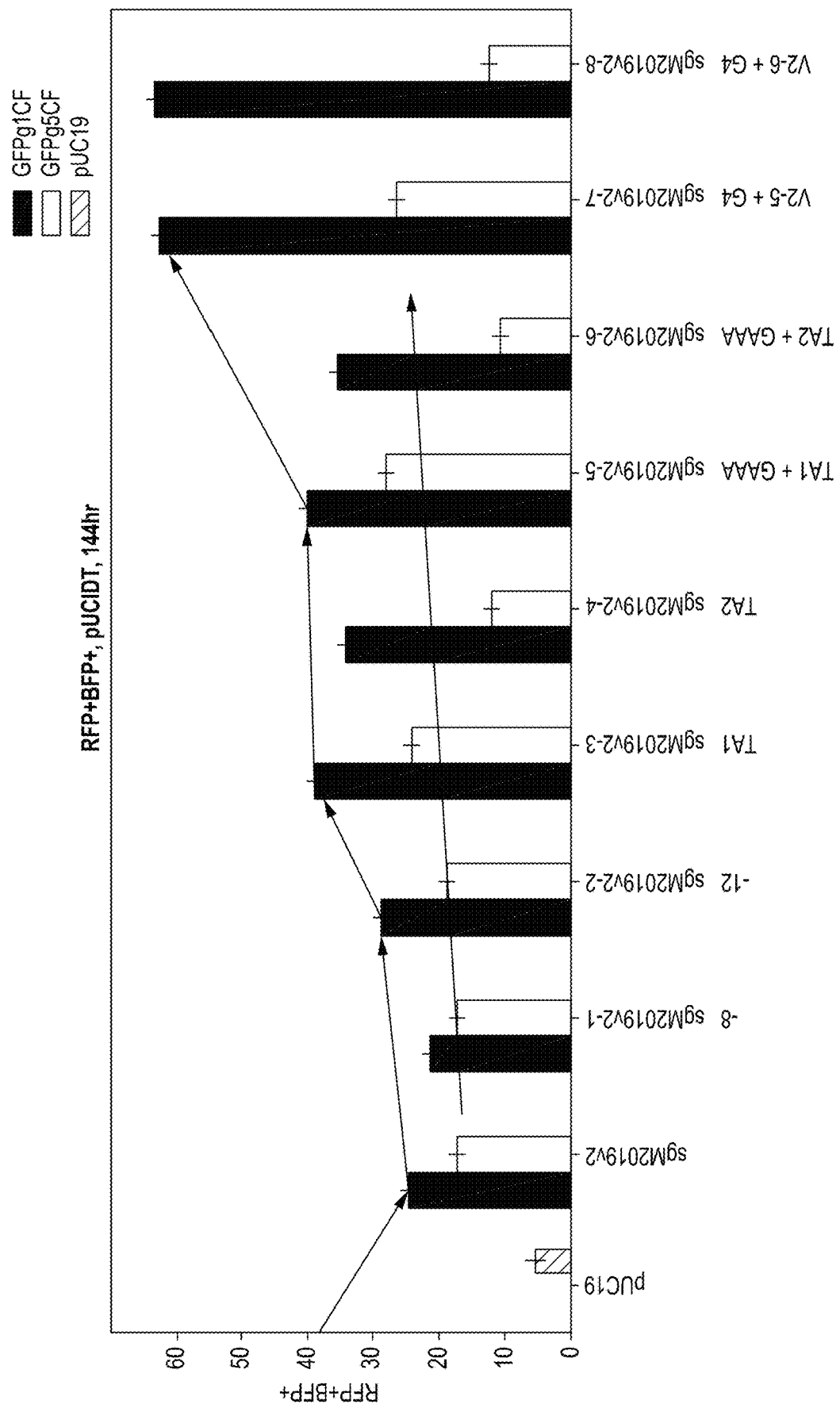
FIG. 5A shows the editing performance of the CF MAD2019 nickase and various scaffolds with two CREATE Fusion (CF) guides and FIG. 5B shows the cut performance of the MAD2019 nuclease and various scaffolds with two CREATE Fusion (CF) guides.
Figure 5B:
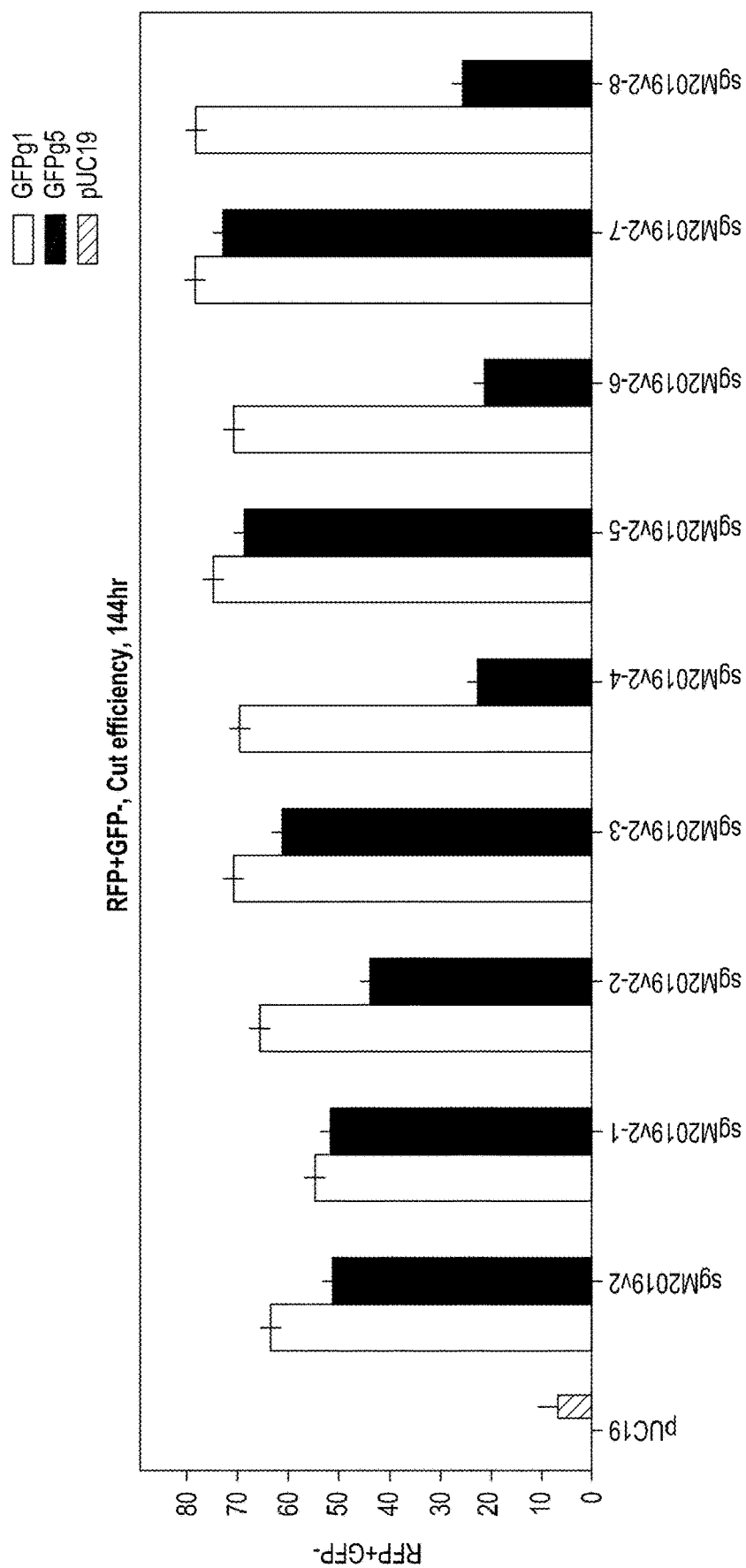

Further Optimization of sgRNA scaffolds: The MAD2019v2 sequence was used to further optimize the sgRNA scaffold. The sequence for each of these variants is shown in Table 5. The full guide comprised from 5' to 3': spacer+sgRNA scaffold (Table 5)+CF (HR in CREATE FUSION column in Table 4)+G4 (if included in the scaffold design) (also in Table 4). The guides were expressed under a U6 promoter. Editing performance using the MAD2019 nickase fused to a reverse transcriptase was measured by performing in vivo editing on the GFP locus in HEK293T cells changing GFP to BFP (see method depicted in FIG. 1B). The BFP signal was measured from cells maintaining an RFP signal after transfection. The results are shown in FIGS. 5A and 5B. In FIG. 5A, performance for each gRNA

TABLE 4

Design of Full Guide: spacer + sgRNA scaffold + HR + G4

| Name of Guide | Guide Sequence | HR in CREATE fusion | G4 |
|---|---|---|---|
| GFPg1CF | GCTGAAGCACTGCACGC CGT [SEQ ID NO: 28] | ACCCTCAGCCACGGCGTGCAGT GCTT [SEQ ID NO: 29] | ACTAACGGTGGTGG TGG [SEQ ID NO: 30] |
| GFPg5CF | GGTGCTGCTTCATGTGGT CG [SEQ ID NO: 31] | ACCCTCAGCCACGGCGTGCAGT GCTTCAGCCGCTATCCCGACCA CATGAAGCAG [SEQ ID NO: 32] | ACTAACGGTGGTGG TGG [SEQ ID NO: 30] |

Two separate plasmids expressing either the MAD nuclease or a guide were transfected into the HEK293T cells with the integrated GFP locus. The coding sequences for the MAD nucleases were expressed under a CMV promoter cloned on a plasmid. The guides were produced from a separate plasmid expressed under the U6 promoter. The expression of the MAD nucleases was measured by an RFP signal produced as a T2A connected self-splicing protein fused to the carboxy terminus of the respective MAD scaffold with the two different CF guides (GFPg1CF (dark bars) and GFPg5CF (light bars)) was measured. Improvement of performance is noticeable with GFPg1CF.

Cutting performance for each sRNA scaffold design with GFPg1CF (light bar) and GFPg5CF (medium dark bar) is shown in FIG. 5B. Cutting performance was measured with wildtype MAD2019 nuclease using the same guide designs used for the CF editing measured with the results shown in FIG. 5A.

TABLE 5

Second Round of Optimization for MAD2019 Nickase

| Sequence Name | Sequence |
| --- | --- |
| sgRNA 2019v2-1 | GTTTTAGAGCTGTGGAAATACAGCAAAGTTAAAATAAGGCTAGTCCGTATACAACGTG AAAACACGTGGCACCGATTCGGTGC [SEQ ID NO: 17] |
| sgRNA 2019v2-2 | GTTTTAGAGCTGGAAACAGCAAAGTTAAAATAAGGCTAGTCCGTATACAACGTGAAA ACACGTGGCACCGATTCGGTGC [SEQ ID NO: 18] |
| sgRNA 2019v2-3 | GTTTAAGAGCTGGAAACAGCAAAGTTTAAATAAGGCTAGTCCGTATACAACGTGAAA ACACGTGGCACCGATTCGGTGC [SEQ ID NO: 19] |
| sgRNA 2019v2-4 | GTTATAGAGCTGGAAACAGCAAAGTTATAATAAGGCTAGTCCGTATACAACGTGAAA ACACGTGGCACCGATTCGGTGC [SEQ ID NO: 20] |
| sgRNA 2019v2-5 | GTTTAAGAGCTGGAAACAGCAAAGTTTAAATAAGGCTAGTCCGTATACAACGTGGAA ACACGTGGCACCGATTCGGTGC [SEQ ID NO: 21] |
| sgRNA 2019v2-6 | GTTATAGAGCTGGAAACAGCAAAGTTATAATAAGGCTAGTCCGTATACAACGTGGAA ACACGTGGCACCGATTCGGTGC [SEQ ID NO: 22] |
| sgRNA 2019v2-7 | GTTTAAGAGCTGGAAACAGCAAAGTTTAAATAAGGCTAGTCCGTATACAACGTGGAA ACACGTGGCACCGATTCGGTGC [SEQ ID NO: 23] + G4 after CF (HR in CREATE FUSION) sequence |
| sgRNA 2019v2-8 | GTTATAGAGCTGGAAACAGCAAAGTTATAATAAGGCTAGTCCGTATACAACGTGGAA ACACGTGGCACCGATTCGGTGC [SEQ ID NO: 24] + G4 after CF (HR in CREATE FUSION) sequence |

Figure 7B:
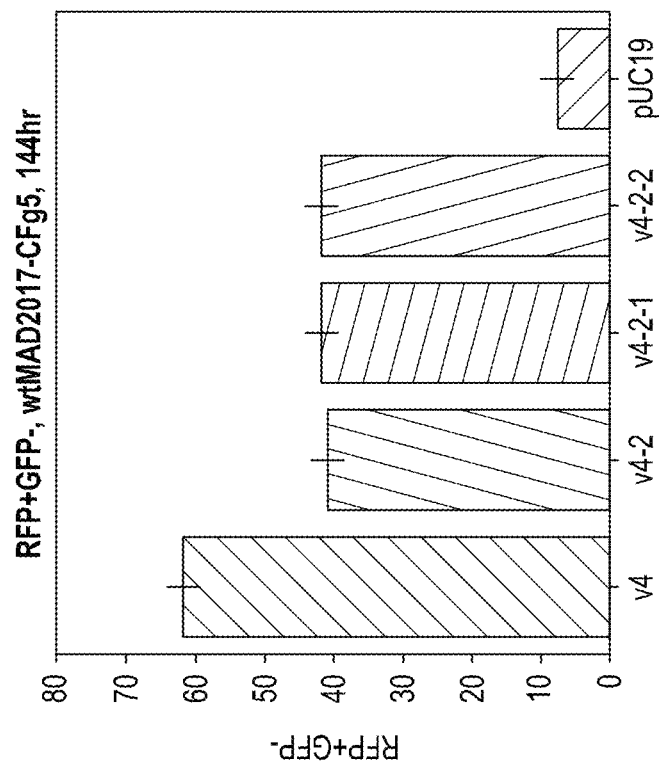
FIGS. 7A and 7B show the cut performance of MAD2017 nuclease and various scaffolds with two CREATE Fusion (CF) guides for cutting activity.
Figure 7A:
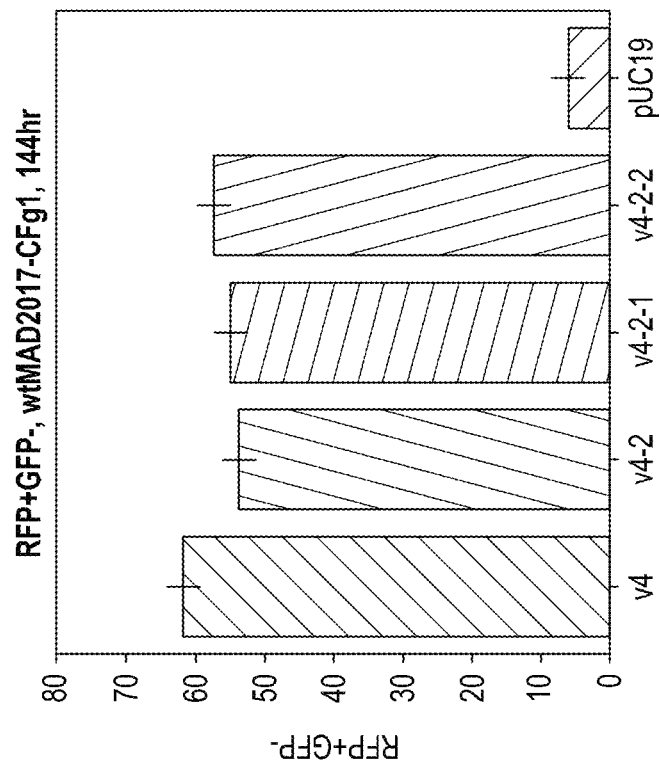

The AD2017v4 sequence was used to further optimize the gRNA scaffold. The sequences for each of these variants is shown in Table 6. The full guide comprised from 5' to 3': spacer+sgRNA scaffold (Table 6)+CF (HR in CREATE FUSION column in Table 4)+G4 (if included in the scaffold design) (also in Table 4). The guides were expressed under a U6 promoter. Editing performance using the MAD2017 nickase fused to a reverse transcriptase was measured by performing in vivo editing on the GFP locus in HEK293T cells changing GFP to BFP (see the method depicted in FIG. 1B). The BFP signal was measured from the cells maintaining an RFP signal after transfection. The results are shown in FIGS. 6A and 6B. Editing performance for each gRNA scaffold was greater for the CFg1 than for CFg5 (GFPg1CF (FIG. 6A) and GFPg5CF (FIG. 6B)); however, cut activity (FIGS. 7A and 7B, GFPg1CF and GFPg5CF, respectively) with the wildtype MAD2017 nuclease indicates the presence of G4 at the 3'-terminal of CF (HR) had the greatest effect. pUC 19 is an empty cloning vector that was used for a negative control for transfection.

TABLE 6

Second Round of Optimization for MAD2017 Nickase

| Sequence Name | Sequence |
| --- | --- |
| sgRNA 2017v4-2 | GTTTAAGAGCTGGAAACAGCGAGTTTAAATAAGGCTTTGTCCGTACACAACTTGTAAA AGGGGCACCCGATTCGGGTGC [SEQ ID NO: 25] |
| sgRNA 2017v4-2-1 | GTTTAAGAGCTGGAAACAGCGAGTTTAAATAAGGCTTTGTCCGTACACAACTTGTAAA AGGGGCACCCGATTCGGGTGC [SEQ ID NO: 26] + G4 after CF (HR in CREATE FUSION) sequence |
| sgRNA 2017v4-2-2 | GTTTAAGAGCTGGAAACAGCGAGTTTAAATAAGGCTTTGTCCGTACACAACTTGAAAA AGGGGCACCCGATTCGGGTGC [SEQ ID NO: 27] + G4 after CF (HR in CREATE FUSION) sequence |

Figure 8A:
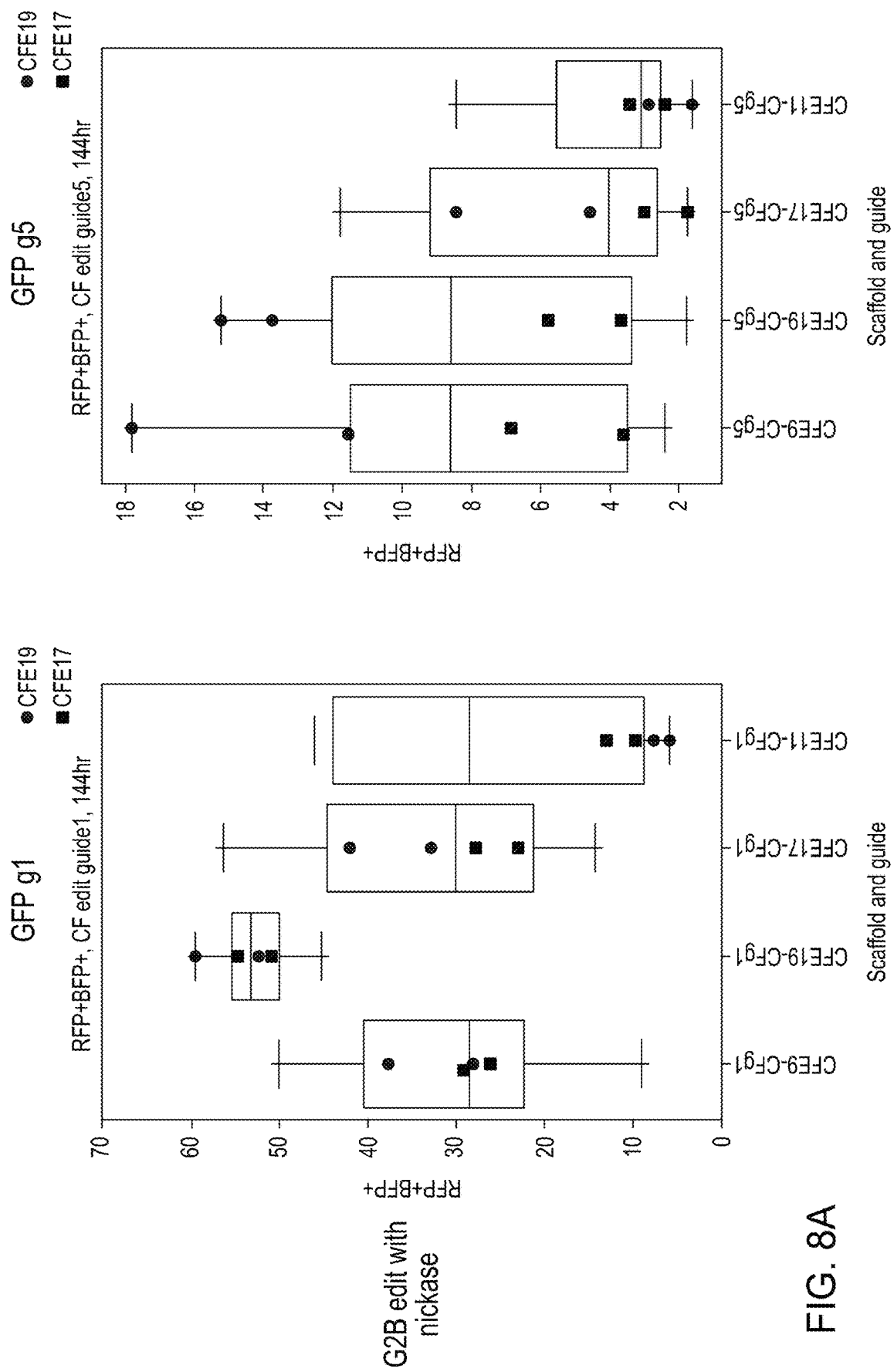
FIG. 8A shows GFP to BFP editing in HEK293T cells comprising an integrated GFP locus using the MAD2017 and MAD2019 nickases.
Figure 8B:
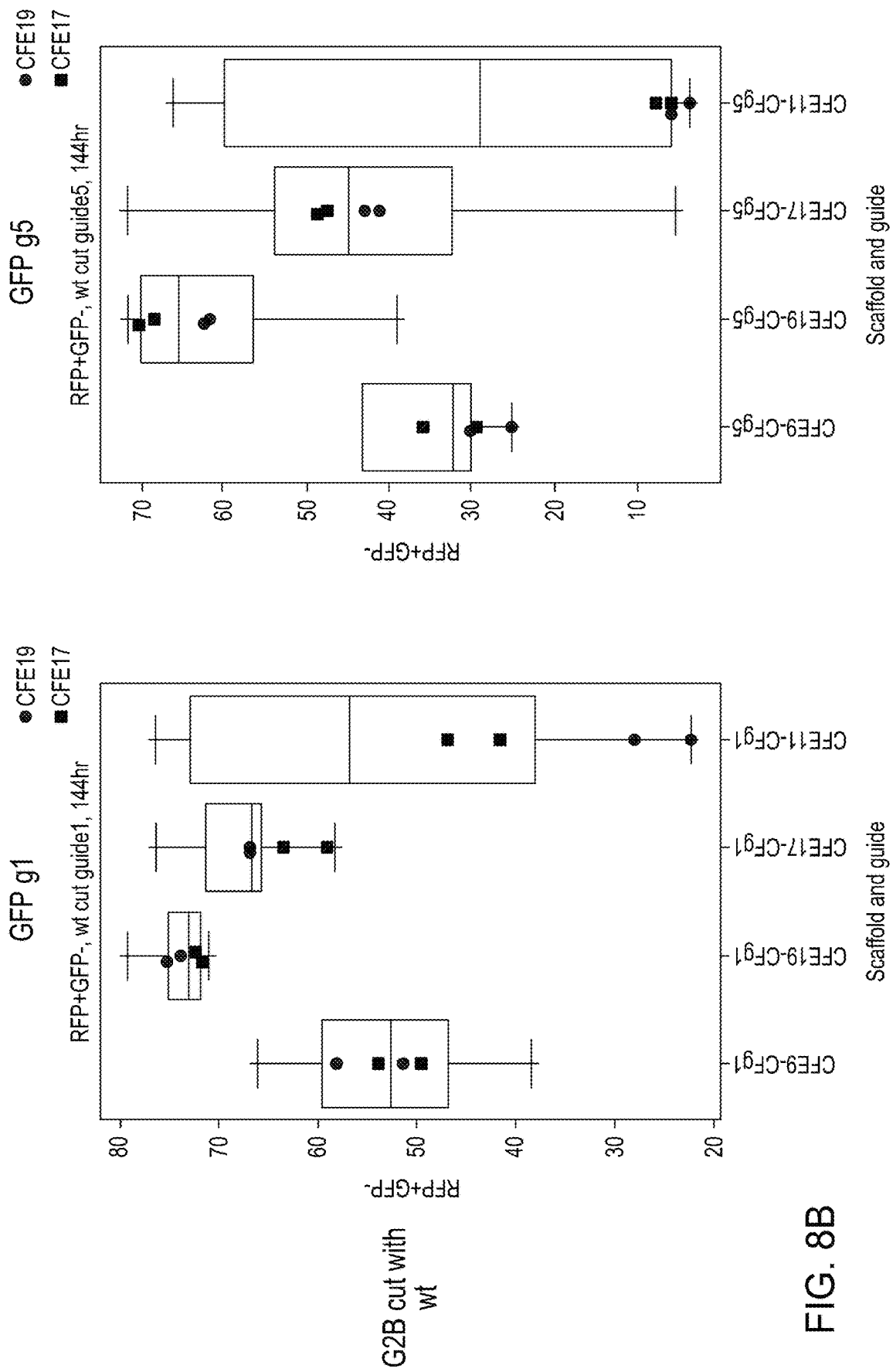
FIG. 8B shows GFP to GFP-cut activity in HEK293T cells with the MAD2017 and MAD2019 nucleases.

Scaffold compatibility between MAD nucleases showed that the gRNA scaffold for MAD2019 was the best universal scaffold for both MAD2019 and MAD2017 wild type and nickases. The results are shown in FIG. 8. FIG. 8A shows GFP to BFP CF editing in HEK293T cells with an integrated GFP locus (GFPg1, left top graph and GFPg5, right top graph). FIG. 8B shows GFP to GFP-cut activity in HEK293T cells with the MAD2019 and MAD2017 nucleases. CFE19-CFg1 had the best universal performance.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A nucleic acid-guided nickase selected from the following nickases: MAD2017-H847A, having the amino acid sequence of SEQ ID NO: 5; and MAD2017-N870A, having the amino acid sequence of SEQ ID NO: 6.

2. The nickase of claim 1 having the amino acid sequence of SEQ ID NO: 5.

3. The nickase of claim 1 having the amino acid sequence of SEQ ID NO: 6.

4. The nickase of claim 1 having the amino acid sequence of SEQ ID NO: 5, in a nucleic acid-guided nickase editing system with a gRNA scaffold having a nucleic acid sequence of SEQ ID NO: 14, SEQ ID NO: 15, SEQ ID NO: 16, SEQ ID NO: 25, SEQ ID NO: 26, or SEQ ID NO: 27.

5. The nickase of claim 4 having the amino acid sequence of SEQ ID NO: 5, in the nucleic acid-guided nickase editing system with a gRNA scaffold having a nucleic acid sequence of SEQ ID NO: 14.

6. The nickase of claim 4 having the amino acid sequence of SEQ ID NO: 5, in the nucleic acid-guided nickase editing system with a gRNA scaffold having a nucleic acid sequence of SEQ ID NO: 15.

7. The nickase of claim 4 having the amino acid sequence of SEQ ID NO: 5, in the nucleic acid-guided nickase editing system with a gRNA scaffold having a nucleic acid sequence of SEQ ID NO: 16.

8. The nickase of claim 4 having the amino acid sequence of SEQ ID NO: 5, in the nucleic acid-guided nickase editing system with a gRNA scaffold having a nucleic acid sequence of SEQ ID NO: 25.

9. The nickase of claim 4 having the amino acid sequence of SEQ ID NO: 5, in the nucleic acid-guided nickase editing system with a gRNA scaffold having a nucleic acid sequence of SEQ ID NO: 26.

10. The nickase of claim 4 having the amino acid sequence of SEQ ID NO: 5, in the nucleic acid-guided nickase editing system with a gRNA scaffold having a nucleic acid sequence of SEQ ID NO: 27.

11. The nickase of claim 1 having the amino acid sequence of SEQ ID NO: 6, in a nucleic acid-guided nickase editing system with a gRNA scaffold having a nucleic acid sequence of SEQ ID NO: 14, SEQ ID NO: 15, SEQ ID NO: 16, SEQ ID NO: 25, SEQ ID NO: 26, or SEQ ID NO: 27.

12. The nickase of claim 11 having the amino acid sequence of SEQ ID NO: 6, in the nucleic acid-guided nickase editing system with a gRNA scaffold having a nucleic acid sequence of SEQ ID NO: 14.

13. The nickase of claim 11 having the amino acid sequence of SEQ ID NO: 6, in the nucleic acid-guided nickase editing system with a gRNA scaffold having a nucleic acid sequence of SEQ ID NO: 15.

14. The nickase of claim 11 having the amino acid sequence of SEQ ID NO: 6, in the nucleic acid-guided nickase editing system with a gRNA scaffold having a nucleic acid sequence of SEQ ID NO: 16.

15. The nickase of claim 11 having the amino acid sequence of SEQ ID NO: 6, in the nucleic acid-guided nickase editing system with a gRNA scaffold having a nucleic acid sequence of SEQ ID NO: 25.

16. The nickase of claim 11 having the amino acid sequence of SEQ ID NO: 6, in the nucleic acid-guided nickase editing system with a gRNA scaffold having the nucleic acid sequence of SEQ ID NO: 26.

17. The nickase of claim 11 having the amino acid sequence of SEQ ID NO: 6, in the system with a gRNA scaffold having a nucleic acid sequence of SEQ ID NO: 27.

18. The nickase of claim 1 having the amino acid sequence of SEQ ID NO: 5, in a nucleic acid-guided nickase editing system with a native CRISPR repeat having a nucleic acid sequence of SEQ ID NO: 12 and a native tracr RNA having a nucleic acid sequence of SEQ ID NO: 13.

19. The nickase of claim 1 having the amino acid sequence of SEQ ID NO: 6, in a nucleic acid-guided nickase editing system with a native CRISPR repeat having a nucleic acid sequence of SEQ ID NO: 12 and a native tracr RNA having a nucleic acid sequence of SEQ ID NO: 13.

20. The nickase of claim 1 having the amino acid sequence of SEQ ID NO: 5 or SEQ ID NO; 4, in a nucleic acid-guided nickase editing system comprising a guide RNA wherein the guide comprises from 5' to 3' a guide sequence, a homology region and SEQ ID NO. 30.

* * * * *